US008613904B2

(12) United States Patent
Everson et al.

(10) Patent No.: US 8,613,904 B2
(45) Date of Patent: Dec. 24, 2013

(54) METHODS FOR DIAGNOSIS AND INTERVENTION OF HEPATIC DISORDERS

(75) Inventors: Gregory Thomas Everson, Englewood, CO (US); Michael Anthony Martucci, Highlands Ranch, CO (US)

(73) Assignee: The Regents of the University of Colorado, Denver, CO (US)

( * ) Notice: Subject to any disclaimer, the term of this patent is extended or adjusted under 35 U.S.C. 154(b) by 259 days.

(21) Appl. No.: 11/814,793

(22) PCT Filed: Jan. 26, 2006

(86) PCT No.: PCT/US2006/003132
§ 371 (c)(1),
(2), (4) Date: May 13, 2008

(87) PCT Pub. No.: WO2006/081521
PCT Pub. Date: Aug. 3, 2006

(65) Prior Publication Data
US 2008/0279766 A1  Nov. 13, 2008

Related U.S. Application Data

(60) Provisional application No. 60/647,689, filed on Jan. 26, 2005.

(51) Int. Cl.
*A61K 51/00* (2006.01)

(52) U.S. Cl.
USPC ........................................ 424/1.37; 424/1.65

(58) Field of Classification Search
USPC ............................................... 424/1.37, 1.65
See application file for complete search history.

(56) References Cited

U.S. PATENT DOCUMENTS

| | | | |
|---|---|---|---|
| 4,207,308 A | 6/1980 | Spenney | |
| 6,778,269 B2 | 8/2004 | Fink et al. | |
| 2006/0067881 A1 | 3/2006 | Groman et al. | |
| 2006/0251576 A1 | 11/2006 | Hellerstein | |
| 2008/0279766 A1 | 11/2008 | Everson et al. | |
| 2010/0055734 A1 | 3/2010 | Everson | |

OTHER PUBLICATIONS

Gilmore et al. "Plasma clearance of oral and intravenous cholic acid in subjects with and without chronic liver disease", Gut, 1980, 21:123-127.*
Denaro et al. "The effect of liver disease on urine caffeine metabolite ratios", Clin Pharmacol Ther 1996, 59:624-635.*
Di Bisceglie (2008) N Engl J Med. Dec. 4, 2008 359(23):2429-41 "Prolonged therapy of advanced chronic hepatitis C with low-dose peginterferon."
Everson et al. (2008) Alimentary Pharmacology & Therapeutics 27:798-809 "The spectrum of hepatic functional impairment in compensated chronic hepatitis C: results from the Hepatitis C Anti-viral Long-term Treatment against Cirrhosis Trial".
Everson et al. (2009) Alimentary Pharmacology & Therapeutics 29:589-601 "Quantitative tests of liver function measure hepatic improvement after sustained virological response: results from the HALT-C trial".
Everson et al. (2009) Hepatology 50(4 Suppl.):1057A, Abstract 1627 "Hepatic Impairment Measured by Quantitative Tests of Liver Function (QLFTs) Predicts Clinical Outcome in Patients with Advanced Fibrosis: Results from the Hepatitis C Anti-viral Long-term Treatment against Cirrhosis (HALT-C) trial".
Gilmore and Thompson (1980) Gut 21:123-127 "Plasma clearance of oral and intravenous cholic acid in subjects with and without chronic liver disease".
Guidance for Industry, Bioanalytical Method Validation, May 2001.
Haque and Yoshida (2009) Annals of Hepatology 8(1):Jan.-Mar: 78-79 "Hepatitis C antiviral long-term treatment against cirrhosis (HALT-C) trial".
Hydzik et al. (2008) Clinical Toxicology 46:1077-1082 "Usefulness of 13C-methacetin breath test in liver function testing in *Amanita phalloides* poisoning: breast feeding woman case".
International Search Report dated Jul. 11, 2007 for PCT/US06/03132.
Koster and Ooms (Dec. 2001) Guide to LC-MS, 3 pp. "Recent Developments in On-line SPE for HPLC and LC-MS in Bioanalysis".
Krumbiegel et al. (Mar. 1990) Eur J Pediatr. 149(6):393-5 "[15N]methacetin urine test: a method to study the development of hepatic detoxification capacity".
Lalazar et al. (Oct. 2008) Journal of Viral Hepatitis 15(10):716-28 "A continuous 13C methacetin breath test for noninvasive assessment of intrahepatic inflammation and fibrosis in patients with chronic HCV infection and normal ALT".
Queiroz and Lancas (Oct. 2004) LCGC North America 22(10).
Renner et al. (1984) Hepatology 4(1):38-46 "Caffeine: A Model Compound for Measuring Liver Function".
Chronic hepatitis data sheet: 2010/2011, Merck, Sharp & Dohme, Corp., 1 page.
Dax, et al., "HPLC-continuous-flow fast atom bombardment mass spectrometry (HPLC-CFFAB)—a convenient method for the analysis of bile acids in bile and serum," Chromatographia, 40(11/12):674-679 (1995).
Decompensated cirrhosis data sheet: 2011, U.S. Department of Veterans Affairs, 1 page.

(Continued)

*Primary Examiner* — Bin Shen
(74) *Attorney, Agent, or Firm* — Merchant & Gould PC

(57) ABSTRACT

The present disclosure concerns methods of administering and detecting a distinguishable agent in a sample from and assessing the condition of an organ in a subject. In a particular embodiment, the present invention concerns methods of detecting and comparing the cholate shunt, in a subject, preferably in a subject with chronic hepatitis C. In certain embodiments, the methods may comprise obtaining a sample from a subject such as a blood or saliva sample after administering an oral and intravenous dose of a distinguishable agent such as cholate and analyzing the sample clearance of the distinguishable agent from the subject and comparing the clearance levels in order to assess hepatic health. In another embodiment, the methods may comprise analyzing a sample from a subject for the presence of a distinguishable agent such as cholate and applying information obtained from analyzing the presence of the distinguishable agent to determine a treatment for a medical condition of the subject.

28 Claims, 7 Drawing Sheets

(56) References Cited

OTHER PUBLICATIONS

Hechey, et al., "Syntheses with stable isotopes: synthesis of deuterium and 13C labeled bile acids," J. of Labelled Compounds, IX(4):703-719 (1973).

Stellaard, et al., "Simultaneous determination of cholic acid and chenodeoxycholic acid pool size and fractional turnover rates in human serum using 13C-labeled bile acids," J of Lipid Research, 25:1313-1319 (1984).

International Search Report and Written Opinion cited in PCT/US2012/040008 mailed Sep. 6, 2012.

Shrestha R, et al., "Quantiative liver function tests define the functional seversity of liver disease in early-stage cirrhosis," Liver Transplantation and Surgery, pp. 166-167, 172, vol. 3, No. 2, Mar. 1997.

Hoofnagle, J., "Course and outcome of hepatitis C," Hepatology, p. S21, vol. 36, No. 5, Nov. 2002.

Denaro, CP et al., "The effect of liver disease on urine caffeine metabolite ratios," Clinical Pharmocology and Therapeutics, pp. 624-635, vol. 59, 1996.

Rector, Jr., WG, et al., "Renal sodium retention complicating alcoholic liver disease: relation to portosystemic shunting and liver function," Hepatology, pp. 455-459, vol. 12, 1990.

Golden, DL et al., "Application of an enzyme-multiplied immunoassay technique for determination of caffeine elimination kinetics as a test of liver function in clinically normal dogs," American Journal of Veterinary Research, pp. 790-794, vol. 55, No. 6, Jun. 1994.

Everson, G.T. et al., "Portal-systemic shunting in patients with fibrosis or cirrhosis due to chronic hepatitis C: the minimal model for measuring cholate clearances and shunt," Alimentary Pharmacology & Therapeutics, pp. 401-410, vol. 26, 2007.

"Qualitative Tests (QLFTS) Detect Impaired Hapatic Function in a High Proportion of Patients with Chronic HCV and Fibrosis or Cirrhosis and May Predict Risk of Cirrhosis, Splenomegaly and Varices," presenation at the 54th Annual Meeting of the American Association for the Study of Liver Diseases, Oct. 2003.

Martucci, "Deconvolutional Analysis on Clearance Curves of Simultaneously Administered Oral and Intravenous Doses of 2,2,4,4-2H Cholate and 24-13C Cholate: Minimal Model to Determine First-Pass Hepatic Extraction of Cholate in Humans," research paper, University of Colorado Health Sciences Center, Aug. 2004.

Invitation to Pay Additional Fees for PCT/US10/47676 mailed Nov. 17, 2010, 2pages.

Medrzejewski, et al., Plasma clearance of cholic acid in patients with chronic diseases of the liver, Polski Tygodnik Lekarski, Apr. 16-30, 1990; 45 (16-18):335-7. Abstract Only, 1 page.

International Search Report and Written Opinion, PCT/US10/47976, dated Feb. 2, 2011, 14 pages.

Extended European Search Report (EP 06734026.5) dated Mar. 31, 2011.

Everson, G. T. et al. (2003): "Quantitative Tests (QLFTS) Detect Impaired Hepatic Function in a High Proportion of Chronic Hepatitis C Patients With Fibrosis or Compensated Cirrhosis and may Predict Risk of Cirrhosis, Splenomegally, and Varices"; Hepatology, vol. 38, Jan. 1, 2003, pp. 304-305.

European Search Report for Application No. 10815965.8 mailed Apr. 17, 2013.

* cited by examiner

METHODS FOR DIAGNOSIS AND INTERVENTION OF HEPATIC DISORDERS

CROSS-REFERENCE TO RELATED APPLICATIONS

This application is a national stage application under 35 U.S.C. §371 of International Application No. PCT/US2006/003132, published as WO2006/081521A2 on Aug. 3, 2006, which has an International filing date of Jan. 26, 2006, which designated the United States of America and which claims the benefit of U.S. Provisional Application Serial No. 60/647,689, filed Jan. 26, 2005, the entire contents of each of which is incorporated herein by reference.

STATEMENT REGARDING FEDERALLY SPONSORED RESEARCH

This invention was made with government support under Grant No. DK092327awarded by the National Institutes of Health. The government has certain rights in the invention.

The present invention relates to methods for assessing hepatic conditions in a subject. In certain embodiments, the disclosed methods may be used to analyze the clearance of a traceable agent introduced to a subject via oral and intravenous introduction as an indicator of hepatic condition.

BACKGROUND

Chronic hepatitis C affects 4 million patients in the United States, and results in 10,000 deaths annually. Major clinical consequences of chronic liver disease are related to the effect of hepatic fibrosis in producing portal hypertension and in the progressive decline of the functioning hepatic mass. Currently, measuring clearance rates of substances primarily removed from circulation by the liver provides the most sensitive, non-intrusive and specific indicator of liver function.

In humans, the two primary bile acids synthesized by the liver are cholic acid and chenodeoxycholic acid, which are converted into secondary bile acids by intestinal bacteria. These bile acids are conjugated with glycine or taurine and secreted by the liver. Serum bile acid levels are determined by the balance between intestinal absorption and hepatic elimination of bile acid.

Cholic acid is an example of a model bile acid. Orally administered cholic acid is absorbed across the epithelial lining cells of the small intestine, bound to albumin in the portal blood, and transported to the liver via the portal vein. Approximately 80 to 85% of cholic acid is extracted from the portal blood in its first pass through the liver. Cholic acid that escapes hepatic extraction exits the liver via hepatic veins that drain into the vena cava back to the heart, and is delivered to the systemic circulation. The area under the curve (AUC) of peripheral venous concentration versus time after oral administration of cholic acid quantifies the fraction of cholic acid escaping hepatic extraction and defines "oral cholate clearance".

Intravenously administered cholic acid, bound to albumin, distributes systemically and is delivered to the liver via both portal venous and hepatic arterial blood flow. The AUC of peripheral venous concentration versus time after intravenous administration of cholic acid is equivalent to 100% systemic delivery of cholic acid. The ratio of the AUCs of orally to intravenously administered cholic acid, corrected for administered doses, defines cholate shunt.

After uptake by the liver, cholic acid is efficiently conjugated to either glycine or taurine and secreted into bile. Physicochemically cholic acid is easily separated from other bile acids and bile acid or cholic acid conjugates, using chromatographic methods.

One NIH-sponsored Hepatitis C Antiviral Long-Term Treatment against Cirrhosis (HALT-C) Trial is examining whether long-term use of antiviral therapy (maintenance treatment) will slow the progression of liver disease. In non-cirrhotic patients who have significant fibrosis, effective maintenance therapy is expected to slow or stop histological progression to cirrhosis as assessed by serial liver biopsies. However, tracking disease progression with biopsy carries risk of complication, possibly death. In addition, sampling error and variation of pathologic interpretation of liver biopsy limits the accuracy of histologic assessment and endpoints. The histologic endpoint is less reliable because advanced fibrosis already exists and changes in fibrosis related to treatment or disease progression cannot be detected. Thus, standard endpoints for effective response to maintenance therapy in cirrhotic patients are prevention of clinical decompensation (ascites, variceal hemorrhage, and encephalopathy) and stabilization of liver function as measured clinically by Childs-Turcotte-Pugh (CTP) score. However, clinical endpoints and CTP score are insensitive parameters of disease progression.

In one proposal, studies were designed to analyze disease progression in a unique subset of patients with chronic hepatitis C, those with fibrosis and early, compensated cirrhosis. These patients are characterized by absence of clinical findings and normal or nearly normal values for standard routine biochemical parameters including serum albumin and prothrombin time. Child-Turcotte-Pugh scores will range from 5 to 6. For this reason, this subgroup of patients may benefit from quantitative tests of liver function that might be more useful than standard biochemical measurements, and more sensitive than clinical endpoints for evaluating the degree and progression of hepatic dysfunction.

Because early intervention of liver dysfunction is critical, a need exists for the detection of early signs that predict the onset or progression of a condition. A number of critical needs could be met by effective and accurate tests of hepatic function.

SUMMARY

The present invention relates to methods for evaluating hepatic condition(s) by correlating clearance levels of detectable agents normally metabolized by the liver. In one embodiment, an exemplary hepatic assay uses a sample from a subject obtained sometime after oral and intravenous administration of a distinguishable agent; at least one oral and one intravenous distinguishable agent is identified. In accordance with this embodiment, the ratio of these agents are compared using a mathematical formula and based on the results the condition of a subject is evaluated. This information may then be used to analyze the condition of a subject, for example the status of the liver. In another embodiment, the ratio of cleared distinguishable agents correlates to the degree of severity of hepatic condition. From such analysis, the propensity for liver failure or disease progression may be determined using the information obtained in one or more samples.

In one embodiment, a sample from a subject with chronic hepatitis C(HCV) may be obtained after administration of an oral and intravenous distinguishable agent sometime there after samples are drawn to access the condition of the subject. In another embodiment, blood samples at different times from a subject with chronic hepatitis C(HCV) may be obtained and analyzed for a detectable agent presence or concentration and this information may be used to assess the condition of the subject. In one example, these samples may be samples that are collected over regular intervals for up but not including 3 hours after introduction of a detectable agent. In another example, these samples may be samples that are collected over regular intervals for up to 1 hour after introduction of a detectable agent. The disclosed methods allow the rapid assessment of organ health of a patient such as the hepatic health of a patient infected with chronic hepatitis C or other liver ailment.

In another embodiment, at least one sample from an intravenous and orally-administered detectable hepatic metabolite-treated subject may be obtained and the levels of detectable hepatic metabolite compared to assess therapeutic intervention. In certain embodiments, blood samples at various intervals from a subject with a hepatic disorder may be obtained to compare the cholate shunt and identify the presence, absence or progression of the hepatic disorder for therapeutic intervention of the condition. In one embodiment, a computer software program may be used to compare levels of the distinguishable agents. In another example, multiple parameters of a subject, such as age and gender, may be examined in combination with the clearance substances to assess the appropriate treatment of a subject. In addition, the criteria may be used to assess the need for administration of a treatment of the subject with at least one therapeutic agent. These assays may be used through-out a therapeutic treatment of the patient in order to continually analyze the progression of the treatment. In another embodiment, these tests may be used in conjunction with other chemical tests in order to gain a more thorough understanding of the overall health of the subject being tested.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

DESCRIPTION OF ILLUSTRATIVE EMBODIMENTS

Definitions

Figure 1:
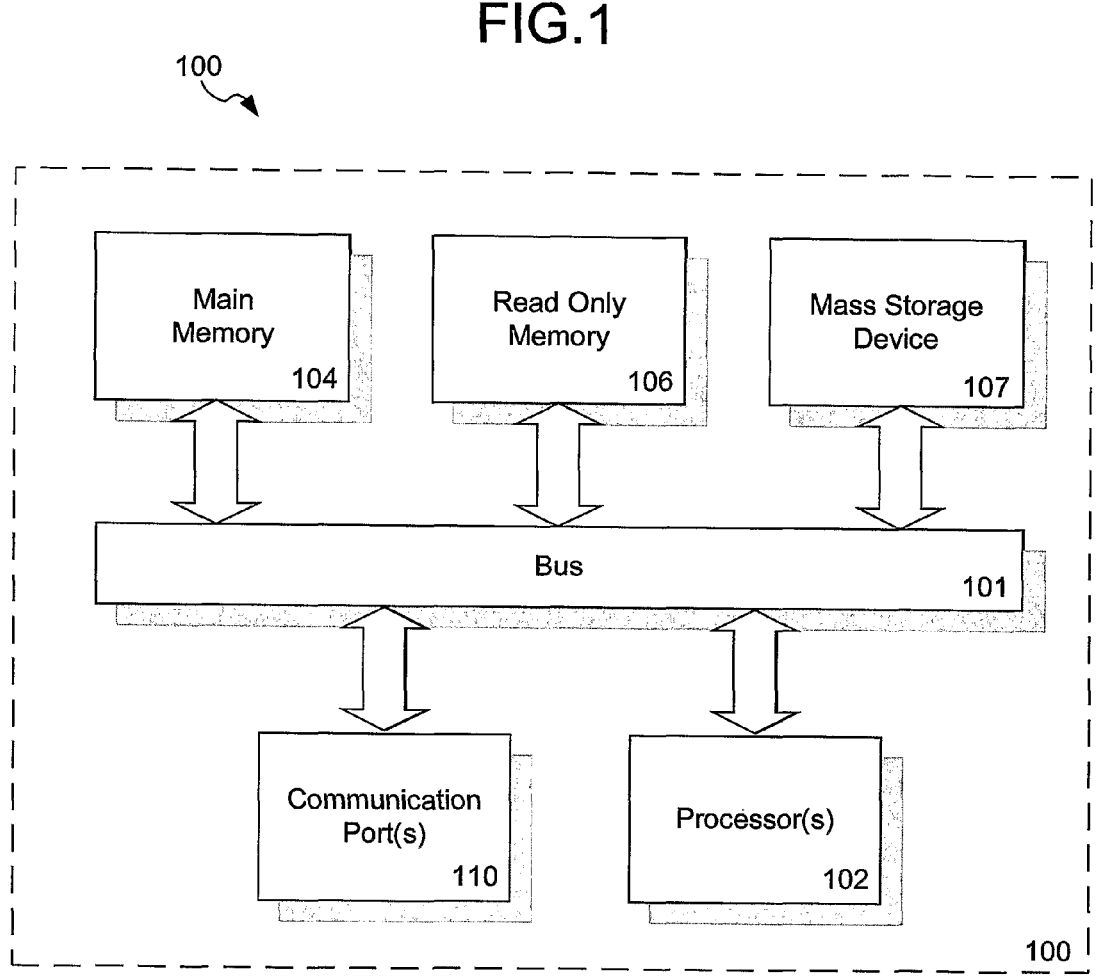
FIG. 1 illustrates an exemplary computing device.

As used herein, "a" or "an" may mean one or more than one of an item. As used herein "clearance" may mean the removing of a substance from one place to another. As used herein the specification, "subject" or "subjects" may include but are not limited mammals such as humans or mammals for example dogs, cats, ferrets, rabbits, pigs, horses, cattle to birds, or reptiles.

DETAILED DESCRIPTION

In the following section, several methods are described to detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description in order to prevent unnecessary masking of various embodiments.

Quantitative Liver Function Tests (QLFTs).

Quantitative Tests (QLFTs), such as assays that measure the liver's ability to metabolize or extract test compounds, may identify patients with impaired hepatic function at earlier stages of disease, and possibly define risk for cirrhosis, splenomegaly, and varices. One of these assays is the cholate shunt assay where the clearance of cholate is assessed by analyzing bodily fluid samples after exogenous cholate has been taken up by the body.

Use of Quantitative Tests of Liver Function to Measure Disease Progression.

Investigators have used the clearance or measurement of metabolites of aminopyrine, antipyrine, bile acids, propranolol, midazolam, dextromethorphan, methionine, methoximine, caffeine, erythromycin, galactose, indocyanine green, lidocaine, and phenacetin to assess hepatic function. Clearances of test compounds are typically defined as dependent upon either hepatic metabolism (aminopyrine, antipyrine, caffeine, erythromycin) or hepatic blood flow (bile acids, indocyanine green). Each quantitative test has advantages and disadvantages over other tests and few studies have compared multiple tests within the same cohort of patients. Studies herein such as QLFTs in HALT-C patients represents a comprehensive comparison of 12 QLFTs, using 8 test compounds, in the same patient. Also, these studies represent patients with chronic hepatitis C and advanced fibrosis using quantitative tests to predict outcome and measuring changes in hepatic function over prolonged periods of time (e.g. 4-6 years).

The most commonly used quantitative tests assess hepatic metabolic capacity. Aminopyrine (dimethylaminoantipyrine) is metabolized primarily by n-demethylation. The hepatic capacity to metabolize aminopyrine can be measured from the specific activity of [14CO2] in breath samples obtained two hours after oral administration of a tracer dose of [14C] aminopyrine. A related compound, antipyrine, is extensively metabolized by a group of cytochrome P450 dependent liver microsomal enzymes, only 5% of the drug appears unchanged in the urine. The plasma or salivary disappearance of antipyrine follows first order kinetics and obeys a simple, one-compartment model. As with all drugs whose clearance is primarily dependent upon metabolism, elimination is not greatly influenced by changes in hepatic blood flow. The main problem with use of these compounds is the reported low rate of severe bone marrow depression, including anemia. There has been one reported fatality due to an overwhelming hypersensitivity reaction in response to a single dose. Antipyrine is also not readily available for use in humans. Phenacetin differs from aminopyrine in that its metabolism is mediated by cytochrome P448 and the [14C] phenacetin breath test is another technique to measure hepatic function in humans.

Caffeine has been used as a test compound for quantitative assessment of the liver because of its relative lack of toxicity, rapid absorption, complete metabolism by the liver, and its ready availability. Caffeine is eliminated by first order kinetics but pathways of metabolism are sometimes extensive and complex. A disadvantage of previous caffeine tests is that caffeine is ubiquitously found in a wide variety of commonly ingested foodstuffs, supplements, and medications; ingestion of caffeine from these sources typically invalidates results of most standard caffeine assays. In addition, the metabolism and clearance of caffeine can be altered by coadministration of drugs or medications.

Erythromycin is eliminated primarily by n-demethylation by hepatic cytochrome P450 enzymes, predominantly CYP3A4 (cytochrome P450 3A4). Numerous xenobiotics, including up to 50% of prescribed medications, are metabolized through the CYP3A4 pathway and may enhance or inhibit erythromycin clearance and metabolism. These effects invalidate the use of erythromycin as a liver function test.

Galactose elimination is complicated by extrahepatic metabolism. Approximately 60% of the total plasma elimination of galactose after a single intravenous injection is due to hepatic clearance; the remaining 40% is due to distribution and metabolism of galactose outside the liver. Thus, galactose elimination capacity is only partially a liver function test.

Other Tests Assess Flow-Dependent Hepatic Clearance.

Indocyanine green (ICG), when administered intravenously is removed from the circulation by the liver with a first-pass hepatic extraction up to 80%. After uptake by the liver, indocyanine green is transported to bile without metabolic transformation. However, as is true of other intravenously administered test compounds, ICG is insensitive and cannot detect early stage disease or small changes in the hepatic condition.

Lidocaine is initially cleared by the liver in a flow-dependent fashion; first pass elimination is up to 81%. Once taken up by the liver, lidocaine is metabolized by oxidative N-demethylation (cytochrome P450 3A4) to monoethyl-glycinexylidide (MEGX). MEGX concentrations are a result of rapid hepatic uptake and clearance from the blood followed by hepatic metabolism and have been used to assess hepatic function in potential liver donors, in liver transplant recipients, and in predicting survival in patients with cirrhosis. Early results suggest that lidocaine-MEGX is useful in assessing short-term prognosis in cirrhotic patients independent of the cause of the underlying liver disease. However, MEGX is subject to the same concerns raised above for intravenously administered compounds (ICG) and its blood level may be affected by interference from coadministered medications, supplements, or dietary factors.

Bile acids are naturally-occurring compounds that exhibit flow-dependent hepatic clearance. Dual isotope techniques allow measurement of first-pass hepatic elimination of bile acids from the portal circulation. Flow-dependent, first pass elimination of bile acids by the liver ranges from 60% for unconjugated dihydroxy, bile acids to 95% for glycine-conjugated cholate. Free cholate, used herein has a reported first-pass elimination of approximately 80% which agrees closely with observed first pass elimination in healthy controls of about 83%. Plasma clearance of oral and intravenous cholic acid in subjects with and without chronic liver disease were studied. These studies demonstrated reduced clearance of cholate in patients who had either hepatocellular damage or portosystemic shunting.

Liver-spleen scans are an effective measure of many parameters affected by chronic liver disease. The liver-spleen scan is useful when the parameters measured are given quantitative expression by SPECT analysis. These parameters can include: 1) precise measurement of sulfur colloid distribution, 2) organ volumes functional 3) organ volumes and/or non-functional volume ratios. Sulfur colloid distribution is determined by Kupffer cell extraction of sulfur colloid and hepatic blood flow. Increased sulfur colloid distribution to spleen and bone marrow is due to either decreased hepatic extraction or decreased hepatic perfusion, both of which are determined by hepatic fibrosis. Thus, precise measurement of this distribution from planar measurement as a redistribution ratio (RR) or from volumetric parameters such as the perfused hepatic mass (PHM) correlate with ICG clearance and other tests of hepatocyte function. In one embodiment, any liver-spleen scan technique known in the art may be combined with any metabolic or clearance assay disclosed herein.

Typically, the PHM remains normal (>100) as scar tissue builds up in the liver until cirrhosis is well established. Once cirrhosis is established the PHM measurement deteriorates proportional to liver disease severity. For example, the PHM range is below the normal range (PHM=100-120) with compensated cirrhosis (PHM=80-110), lower still with ascites and variceal bleeding (PHM=40-80), and generally less than sixty in cirrhotic patients who die or require transplant. The non-fibrotic mass (functional hepatic mass) in a group of cirrhotic patients whose liver was removed at transplant or autopsy correlated closely with the PHM (correlation coefficient 0.95).

Areas of critical need for noninvasive QLFTs include, but are not limited to the following: detection of fibrosis and early cirrhosis (e.g. to avoid liver biopsy); detection of risk of varices (e.g. identification of patients who might benefit from endoscopy therapy); assessment of likelihood to respond to antiviral therapy (e.g. more refined selection of patients for treatment); defining level of hepatic impairment prior to treatments that might affect or could be affected by liver function (e.g. more precise definition of the level of hepatic impairment, selection of patients for transjugular intrahepatic portal-systemic shunt (TIPS) placement, or defining impairment prior to institution of chemotherapeutic agents to treat cancer; tracking disease progression. (e.g. early detection of decompensation); and measure effects of therapies or interventions (e.g. The changes in QLFTs may occur long before clinical deterioration and, QLFTs would have increased sensitivity at detecting changes in the hepatic condition induced by the treatment/intertervention, a smaller sample size could be utilized in defining effects).

Combination Tests Quantitative Tests of Liver Function (QLFTs).

Comprehensive assessment of functional hepatic reserve may require one reliable quantitative test or a combination of quantitative liver function tests. However, few, if any, studies have compared the results of more than two tests within the same cohort of patients largely because of the complexity of some of the tests.

In one study herein, QLFTs in HALT-C patients were examined for the utility of multiple QLFTs in predicting cirrhosis and varices. These analyses indicated that cholate shunt and oral cholate clearance were useful and complementary to standard clinical assessment in prediction of both cirrhosis and varices. In addition, QLFTs correlated not only with clinical and laboratory measures of hepatic function but also predicted response to antiviral therapy. One advantage of these tests is the use of a combination of quantitative tests to comprehensively define hepatic function in selected and controlled populations. These tests provide critical information necessary for the understanding of functional hepatic capacity and recovery for the most if not all liver conditions.

One Quantitative Test for Hepatic Condition

Cholate Clearance:

Clearance of cholate is dependent upon specific high-affinity transport proteins located on the sinusoidal surface of hepatocytes and is proportional to hepatic blood flow and hepatocyte function. Clearance of cholate from portal blood or first-pass hepatic extraction, can be measured in humans using dual isotopes (e.g. stable isotopes) and simultaneous oral and intravenous administration. Stable ($^{13}$C, $^{2}$H, $^{15}$N, $^{18}$O) or radioactive isotopes ($^{14}$C, $^{3}$H, Tc-99m) can be used. Advantages of stable isotopes are the lack of exposure to radioactivity, natural abundance, and the specificity of the analyses used for test compound identification (mass determination by mass spectrometry). Cholate escaping hepatic extraction enters the systemic circulation and is defined as the cholate shunt. In patients in the previously mentioned HALT-C trial, cholate shunt correlated with for example cirrhosis on liver biopsy, varices on endoscopy, splenomegaly on ultrasonography, platelet count (a reflection of infection), and biochemical markers of disease severity. In this study the method of measuring the cholate shunt required sampling of blood for at least 3 hours resulting in prolonged discomfort and delay to the patient.

Improvements to the Test:

In one embodiment a cholate clearance test may be used alone or in combination with other hepatic assessment tests. One Quantitative Liver Function Tests (QLFTs), a cholate shunt test determines a relative value for predicting clinical outcome or monitoring of hepatic disease progression. In one embodiment of the invention, 13C-cholate may be administered intravenously and 2H4-cholate may be administered orally to a subject suspected of having or developing a liver disorder. In accordance with this embodiment, blood samples for measurement of cholate isotopes may be obtained at a baseline and several times after the baseline. For example samples may be taken at 5, 10, 15, 20, 30, 45, 60, 75, 90, 105, 120, 150 and less than 180 minutes post-dose where a total of 14 blood samples may be collected over 180 minutes. Alternatively, fewer samples may be obtained such as samples up to a half an hour after administration of cholate. From these samples, intravenous and oral cholate clearance curves can be generated. The least squares method can be used to determine the area under the cholate clearance curves. Next, the liver shunt fraction, an indicator of liver function, is calculated using a method described in the Exemplary Operations section.

In order to reduce patient discomfort, time and resources, in one embodiment a deconvolutional analysis may be used to generate intravenous and oral distinguishable agent clearance curves. To assess one or more hepatic conditions in a subject in the optimal amount of blood draws and time, spline functions, calculated elimination rates and direct integration of mathematical equations may be used to reduce the number of blood draws and reduce the time required for assessment.

Each of the above tests has certain advantages and disadvantages but few studies have examined the value of quantitative tests or compared the relative benefits of individual tests in either predicting disease progression or in monitoring response to long-term maintenance therapy. The present invention proposes quantitative tests that may predict outcome and therapeutic endpoints, in subjects with a liver condition (e.g., chronic hepatitis C with compensated cirrhosis).

In an earlier study, hepatic function was compared between Childs-Turcotte-Pugh A cirrhotics and normal controls by measuring the clearances of antipyrine, caffeine, and cholate labeled with stable isotopes, and cholate shunt. First, Childs-Turcotte-Pugh A cirrhotics were chosen because use of QLFTs to quantify the degree of hepatic impairment in cirrhotics with obvious clinical deterioration (Childs-Turcotte-Pugh B and C) was assumed to be of little additional utility above standard liver tests and clinical assessment. Second, the existing literature suggests that Childs-Turcotte-Pugh A cirrhotics likely have a wide range of hepatic functional impairment ranging from nearly normal to severely abnormal making this condition ideal for studying functional differences by QLFTs. Quantitation of liver function within this group might yield cutoffs for test results more likely to predict subsequent clinical outcome. Third, the use of multiple tests allowed comparison of the predictive value of a number of quantitative tests. Specifically, these test may provide whether compounds cleared by hepatic metabolism including, but not limited to, for example caffeine and antipyrine or those whose clearance was flow dependent including but not limited to cholate, lidocaine, inderol, and nitroglycerine are informative with respect to functional reserve and risk of decompensation.

These studies revealed that the hepatic clearances of the administered compounds were significantly reduced in patients with cirrhosis but the range of functional impairment overlapped into the range of healthy controls. Five patients decompensated and required hepatic transplant or died from liver failure. Caffeine elimination or antipyrine clearance failed to separate these 5 patients from the cirrhotics who remained stable.

In contrast, the clearance of orally-administered cholate and first-pass elimination of cholate (cholate shunt) correlated with the patients who ultimately demonstrated evidence of decompensated liver disease during the follow-up period. The values for oral cholate clearance and cholate shunt in decompensated patients differed from the values measured for stable patients. These results indicated that quantitative tests, in particular dual cholate clearance, identified Childs-Turcotte-Pugh Class A cirrhosis patients at greatest risk for decompensation. Although the study focused on CTP Class A patients, the results may also be valid for patients with more advanced disease (CTP Class B or C) especially in prediction of severe complications (ascites, variceal hemorrhage, encephalopathy), hepatoma, or need for transplantation.

Thus, in one embodiment of the present invention, patients with Childs-Turcotte-Pugh Class A (and possibly CTP class B or C) cirrhosis may be tested for hepatic health. In a more particular embodiments, the cholate shunt assay detailed herein may be used to evaluate patients with Childs-Turcotte-Pugh Class A cirrhosis to analyze hepatic health. In another embodiment, a dual cholate clearance and shunt test may be used to evaluate patients with Childs-Turcotte-Pugh Class A cirrhosis to analyze hepatic health. In another embodiment, a dual cholate clearance and shunt test may be used to evaluate patients with Childs-Turcotte-Pugh Class A cirrhosis to analyze hepatic health in order to assess the need for therapeutic intervention. Alternatively, a cholate shunt assay and/or an oral cholate clearance assay may be used to assess hepatic health of a subject undergoing a therapeutic treatment for a liver condition such as, but not limited to, Childs-Turcotte-Pugh Class A cirrhosis.

Quantitative testing of hepatic function is useful for predicting outcome in a subject with fibrotic liver disease otherwise clinically stable with no biochemical or clinical decompensation. In addition, quantitative tests are useful as therapeutic assessments in patients who have mild hepatic dysfunction around baseline and who achieve a positive therapeutic response. In addition, QLFTs may also measure rate of disease progression during the course of a trial where lack of response or failure to receive therapy is likely to further impair hepatic function.

Example Methods:

Isotopically Labeled Cholate Administration:

In one exemplary method about 20 mg of 24-13C cholic acid was dissolved in NaHCO3, mixed with 5 ml 25% human albumin and injected through an intravenous catheter over 2 min. In another exemplary method about 40 mg of 2,2,4,4-2H cholic acid was dissolved in water and taken orally. In one example, blood was drawn at baseline and 5, 10, 15, 20, 30, 45, 60, 75, 90, 105, 120, 150 and less than 180 minutes post-dose. In one exemplary method, the cholates were isolated by extraction from serum with Sep-Pak C18 cartridge, acidification, ether extraction, methylation, TMS derivatization and capillary GC/MS isotope ratiometry. In one exemplary method, the Cholate shunt may be calculated as AUC-oral/AUCiv×Doseiv/Doseoral×100%.

General Considerations for the Cholate Shunt

In one embodiment, the present invention concerns detecting cholate in a sample of a subject for prediction of the onset or progression of a hepatic condition.

Healthcare providers are in need of an accurate and relatively inexpensive and easily administered test for early predictors of organ failure. In one example, a quick test for the prediction of hepatic health is needed. In other examples, a quick, accurate, and relatively inexpensive test for the prediction of liver failure is needed. Because of the nature of cholate as a predictor of hepatic health of a patient such as a patient with a liver condition (e.g., chronic hepatitis C), a method that can alert a healthcare provider that hepatic health is worsening or improving with treatment would be beneficial from a clinical perspective. This information can alert the health care provider that intervention by a therapeutic treatment may be required immediately. The application of such methods is important for patients with a propensity for organ failure such as hepatic failure, for example in chronic hepatitis C patients. In addition, the application of such methods is important for patients undergoing organ transplantation such as liver transplantation. Other situations where these techniques may be useful include kidney, lung, heart and bone marrow transplantations. Any disease that might alter the hepatic condition could be an indication for use of the test.

Methods for detection of cholate clearance in a sample are disclosed herein. A relatively cheap, quick and reliable assay will promote optimal application of a health provider's resources to diagnose organ insufficiencies such as hepatic insufficiencies and other conditions of altered hepatic function Alternatively, a quick and reliable assay such as methods for detection of cholate clearance in a sample may be used to monitor response to drug regimen and assess treatment efficiency, leading to a decreased loss of life and decreased cost. These methods may be used to assess the efficiency of one therapeutic treatment versus another or comparing various dose levels of the similar or different treatments on a patient suffering from a hepatic condition.

Advantages of the cholate shunt assay include reliable results that correlate with organ health (e.g. liver health) and use of a naturally occurring substance rather than a drug in a variety of subjects bearing or predisposed to an organ condition. Because the assay utilizes accurate and specific detection methods, the reproducibility and reliability of the test will provide accurate sample analysis. The equipment and methodologies used to analyze the presence of cholate may require chromatography (GC or HPLC) and mass spectrometry with appropriate training of the operator. However, the assay does not require any unusual or complex techniques outside the general spectrum of assays utilizing GC/MS or HPLC/MS technology. The assay is straightforward since the introduced cholate is distinguishable. The assay is sensitive and requires a short time period, typically in the time range of 90 minutes or less. Since the cholate shunt assay can be used to measure cholate clearance early in disease progression and may be combined with other assays, it provides more complete data than presently used methods for early intervention and treatment of hepatic conditions.

The evaluation of the presence of distinguishable cholate in the context of other parameters has suggested that the cholate shunt assay is sensitive to altered states of organ health, including liver in critically ill patients.

Because of the vital importance of earlier targeting of therapies in a shorter amount of time, many markers have been explored for early diagnosis of hepatic disease or condition. An assay requiring 3 hours or longer causes increased discomfort to a subject undergoing such a test.

Uses of Cholate Shunt Assay

Cholate Shunt Assay:

In some embodiments, cholate shunt assay results may be analyzed in an individual having or predisposed to a liver condition. Non-limiting examples of liver conditions include but are not limited to cirrhosis, splenomegly, varices, cancer and chronic hepatitis C infection.

In an another embodiment, cholate shunt assay results may be analyzed in an individual undergoing an organ transplant. Non-limiting examples of organ transplants include but are not limited to liver transplant rejection, delayed function of the liver transplant, recurrent disease in the transplanted graft, and liver injury.

In yet another embodiment, the cholate shunt assay may be used to analyze healthy subjects to assess organ health in steady state and in times of altered (pathologic or physiologic) conditions, including the special physiologic states of organ transplant.

Evaluating and Monitoring the Clearance of Cholate

Whether or not organ (or cellular) destruction can be minimized after events such as organ injury or prolonged exposure to an infection (e.g., Hepatitis C) may depend, in part, upon the early introduction of therapeutically relevant treatments. In order to eliminate, minimize or attenuate such destruction in an individual who has undergone or is undergoing organ damage, failure or similar event, it would be helpful to predict these events earlier in progression rather than later. By comparing the individual's specific level of clearance of cholate to a normal healthy control, or within a given individual over time, a treating physician might determine whether the subject needs to be treated immediately or otherwise observed for a period of time.

Under conditions when cholate clearance is detectably altered in a sample of a subject, such as after organ injury, organ transplant or prolonged infection, it becomes critical that the treating healthcare provider have reliable information available about an individual's concentration of cholate in the sample. For example, a relatively high concentration of the orally administered cholate in the blood is especially likely to occur when the subject is undergoing a delayed liver transplant graft function. In addition, a relatively high concentration of orally administered cholate in the blood is especially likely to occur when a subject with a liver condition (e.g., Hepatitis C) has experienced hepatic insult. Thus, when a patient's organ activity such as hepatic activity is impaired as indicated in the examples above, a healthcare professional may intervene and administer a therapeutic treatment to attenuate the condition or possibly reverse failure of the organ. Theses interventions may avoid permanent damage or death of the patient. In addition, a healthcare professional may monitor the therapeutic treatment of the subject by obtaining samples from the patient after treatment and analyzing the presence of cholate in the sample and assessing the condition of the patient based on these findings. Therapeutic treatments may be altered depending on the change in cholate detection or concentration of cholate present in the sample.

Healthcare professionals have been hindered by an inability to prescribe individualized doses of agents tailored to the unique physiological responses of a particular subject early enough in the process of organ failure. In the absence of such data, most treatments are introduced to a patient too late. Early diagnosis and intervention with a treatment such as introduction of fluids, sodium bicarbonate, atrial natriuretic peptides, growth factors, dialysis, or any therapy for prevention of organ failure may either attenuate the progression of the condition or alleviate the symptoms of the condition. Thus, a rapid test to assess the onset of organ failure would be extremely useful for diagnosis and therapeutic monitoring. In one embodiment, hepatic health of a subject may be monitored using a dual cholate assay disclosed herein. In accordance with this embodiment, therapeutic intervention may be administered to the subject as necessary. In another embodiment, hepatic health of a subject undergoing therapeutic intervention may be assessed using a dual cholate assay disclosed herein.

Methods:

EXAMPLES

Example Protocols for Quantitative Testing

Participants can undergo quantitative assessment of hepatic functional reserve at baseline, and in follow-up at 2 and 4 years of the maintenance treatment protocol. At each time point, quantitative testing will be performed after 3 days of a caffeine-free diet and an overnight fast. Patients can report to their respective treatment centers and be admitted to the respective clinical research center. An indwelling catheter will be placed in an antecubital vein and baseline blood drawn. Test compounds can be administered both orally (i.e. 2H4-cholate, caffeine, antipyrine) and intravenously (i.e. 13C-cholate, galactose, lidocaine).

Intravenous 13C-cholate, 20 mg, is dissolved in $NaHCO_3$ solution, passed through a micropore filter, and placed in sterile, capped glass vials prior to use. This preparation can be mixed with 5 ml of 25% human albumin solution just prior to intravenous injection. In one example, blood samples for measurement of cholate isotopes can be obtained at baseline and 5, 10, 15, 20, 30, 45, 60, 75, 90, 105, 120, 150, and less than 180 minutes post-dose (14 samples, 7 ml red top tubes).

In one example, a Galactose (30% solution), 100 ml, is given intravenously over 5 minutes. Blood is obtained at 20, 40, 60, and 80 minutes post-dose (7 ml gray top tubes). Samples must be kept on ice or refrigerated. Spin samples for 10 min at 3000 rpm, remove plasma and keep at −200 C until analysis. "High-dose" samples are diluted 1:2 in Milli-Q water before testing.

The standard test dose for intravenous infusion of lidocaine in the MEGX (monoethylglycine zylidide) assay is 1 mg/kg over 2 minutes. However a recent report suggested that a lower dose (less than 1 mg/kg such as 0.5 mg/kg) may be better tolerated, associated with fewer side effects (30 vs. 53%, sensory symptoms), and gives similar accuracy in quantitating hepatic function. In this experimental example 0.5 mg/kg dose will be used in this study. Blood is obtained at baseline and 15 minutes post-infusion. Results are reported as the difference between the concentrations of MEGX at 15 minutes post-lidocaine, compared to concentration at baseline.

In one exemplary method, saliva samples, for measurement of antipyrine and caffeine, will be obtained at baseline and at 6, 12, 24, 36, 48, and 60 hours post-dosing (7 samples, 5 mls each).

Other Quantitative Tests

Antipyrine and Standard Caffeine Test (saliva). In another exemplary method, salivary samples are centrifuged to remove particulates, dispensed into 1 ml aliquots for analysis, and internal standard (phenacetin) added. After extraction with organic solvent, samples can be quantitated using HPLC (WISP system). Kinetic parameters (kelim, Vd, Cl) can be calculated from the plot of salivary concentration vs. time. Concentrations of antipyrine in saliva are equivalent to that found in plasma and all kinetic parameters for antipyrine can be determined from saliva. Kelim is equivalent from saliva and plasma. In contrast, albumin binding of caffeine reduces the diffusion of caffeine into saliva and caffeine concentrations are, therefore, lower in saliva Because this effect can lead to falsely high Vd and apparent clearances for salivary caffeine, compared to the same parameters determine from serum samples new and improved methods for assessing caffeine clearance might be beneficial. Kelim from the caffeine data and kelim, Vd, and Cl from the antipyrine data will likely be used.

Liver Metabolism Test:

In one embodiment, hepatic condition of a subject may be assessed using a test including an agent labeled by two or more different distinguishable agents. These distinguishable agents may be introduced to a subject at different times and different dosages and metabolically tracked in the subject. In accordance with this embodiment, the distinguishable agents may include different distinguishable isotopes (e.g. stable isotopes: 13C, 2H, 15N, 18O or radioactive isotopes 14C, 3H) linked to for example, an agent readily metabolized by the liver such as caffeine. Distinguishable caffeine can be purchased (for example CDN Isotopes Inc., Quebec, CA). This test is referred to as a multi-isotope caffeine metabolism test. To assess hepatic condition in a subject, distinguishable caffeine may be introduced orally and/or by IV and introduced to a subject over a period of time. After introduction to the subject, distinguishable caffeine metabolites are tracked by assessing saliva and/or blood samples. In one embodiment, hepatic condition of a subject may be assessed using 3 different isotopically distinguishable caffeine solution (triple isotope method: TIME) introduced to a patient and sometime later obtaining saliva and/or blood samples where metabolism of the solution is indicative of the subject's hepatic condition. It is contemplated that the time of administration of the distinguishable agent may vary from as short as a few hours to as many as 36 hours before a sample is obtained and metabolism assessed. In one particular embodiment, each distinguishable caffeine solution may be introduced to a subject at a different time and one saliva or one blood sample obtained from the subject sometime after administration of all caffeine solutions to the subject.

In another embodiment, hepatic condition of a subject may be assessed using a test including caffeine labeled by two or more distinguishable agents, introduced to a subject and metabolically tracked in the subject in combination with another hepatic assessment test such as a hepatic blood flow test. For example the multi-isotope caffeine metabolism test (e.g. triple isotope method) may be combined with a cholate clearance or cholate shunt test disclosed herein. Other tests may be combined with the multi-isotope caffeine metabolism test such as other metabolism or hepatic blood flow tests that reflect hepatic condition. Outcome of these tests are indicative of hepatic condition and thus assessment of current or future need of treatment to alleviate any hepatic condition in a subject may be recognized. In addition, any methods disclosed herein may be used to assess hepatic condition in a subject undergoing a treatment for a condition. If required, a treatment of such as subject may be modified in accordance with the hepatic condition.

In the present invention, one advantage of using a multi-isotope caffeine test is that dietary caffeine will not interfere with the assay. In addition the data obtained from elimination of caffeine from an individual is near total elimination of the caffeine. The sampling post administration of the distinguishable solution may be a single time point.

Unlike the typical clearance, metabolism, or breath test analyses of caffeine, caffeine tests disclosed herein avoid caffeine interference by diet or drug caffeine. In addition, caffeine tests of the present invention assess a more global assessment of caffeine metabolism compared to traditional caffeine breath tests that assess a single pathway.

Example of Establishing the Predictive Value of Quantitative Tests.

In one embodiment, the results of the baseline studies will be characterized by one or more of a mean, median, distribution, and confidence intervals for each of the measures of hepatic function (caffeine kelim, antipyrine kelim, antipyrine Vd, antipyrine clearance, galactose elimination capacity, MEGX15 min, cholate kelim iv, cholate Vd iv, cholate Cliv, cholate Clpo, cholate SF, and perfused hepatic mass). The median value for each test may be used to divide the patient sample into two groups for analysis of the ability of the test to predict clinical progression. The composition of the groups will change for each test analyzed based upon the baseline results for the specific test undergoing evaluation. For example, the median value for caffeine kelim may be 0.04 h-1. Values below 0.04 h-1 indicate poorer function and greater likelihood for early clinical decompensation. The median value for cholate SF may be 30%; values above 30% indicate poorer first-pass clearance and greater likelihood for early decompensation. Patient A tests may indicate caffeine kelim 0.06 $h^{-1}$ and cholate SF 55%. In the analysis of the predictive value of these tests, his long-term outcome would be analyzed with the caffeine group likely to have a better outcome but with the cholate group likely to have a poorer outcome. Predictive value is calculated by standard technique using 2×2 tables that define true positives (TP) and negatives (TN) and false positives (FP) and negatives (FN). A hypothetical analysis is shown for the example of results from cholate SF testing:

| Disease Progression | Cholate SF >30% | Cholate SF <30% |
| --- | --- | --- |
| Yes | TP | FN |
| No | FP | TN |

Positive Predictive Value = TP/[TP + FP] × 100%
Negative Predictive Value = TN/[TN + FN] × 100%

The predictive value of the various tests may be compared and interaction between the quantitative tests in predicting outcome will be performed by multivariate analysis of the continuous independent variables (quantitative tests) against the binomial dependent variable (development or absence of clinical decompensation).

Example Control Groups:

Quantitative Tests as an Outcome or Endpoint of Therapy.

The control group of a given study may experience progressive decline in hepatic function as measured by quantitative tests. Each patient may serve as his own control; test results in years 2 and 4 of treatment will be subtracted from baseline test values. The absolute and percent change from baseline will be determined for each patient at each time point and mean, median, distribution, and confidence intervals determined. Statistical significance of differences in the changes from baseline between treatment and control groups may be determined by ANOVA. In addition, changes in quantitative tests will also be compared to changes in fibrosis scores, fibrosis morphometry, standard biochemical tests, and concentrations of HCV RNA. Kaplan-Meier curves and Log-Rank tests (nonparametric) will also be used to compare the changes in quantitative tests between the two patient groups.

Other Tests for Combination Analysis:

Sulfur Colloid Distribution Parameters

In one exemplary method, the cholate shunt analysis may be combined with analysis of sulfur colloid distribution. The distribution of sulfur colloid from the planer scan can be assessed by any means known in the art. In another example, distribution of sulfur colloid between liver and bone marrow may be assessed by any means known in the art and used in combination with any assay disclosed herein.

Distinguishable Compounds:

Distinguishable compounds, agents or solutions used herein may include compounds that are traceable or trackable. These compounds linked to an agent of interest (e.g. cholate or caffeine) may be followed as they are processed or passed through a subject before, during and/or after administration of the distinguishable agent to the subject. Cholates used in any one of these assays might be labeled with either stable (13C, 2H, 18O) or radioactive (14C, 3H) isotopes. These same isotopes and potentially 15N or Tc-99m could be linked to any of the other agents described and referenced herein. A number of other test compounds listed in the descriptions above and could be used as potential substitutes for either cholate (other bile acids, propranolol, lidocaine, nitroglycerin) or caffeine (antipyrine, erythromycin, lidocaine-MEGX, midazolam, dextromethorphan, and any other xenobiotic or compound metabolized by the P450 system).

A radionuclide may be bound to an agent such as cholate either directly or indirectly by using for example an intermediary functional group. Intermediary functional groups which may be used to bind radioisotopes which exist as metallic ions to antibody are diethylenetriaminepentaacetic acid (DTPA) and ethylene diaminetetracetic acid (EDTA). Examples of metallic ions suitable for use in this invention are 99 mTc, 123I, 131I 111In, 131I, 97Ru, 67Cu, 67Ga, 125I, 68Ga, 72As, 89Zr, and 201Tl.

In accordance with these embodiments, agent(s) thereof may be labeled by any of several techniques known to the art. The methods of the present invention may also use paramagnetic isotopes for purposes of in vivo detection. Elements particularly useful in Magnetic Resonance Imaging ("MRI") include 157Gd, 55Mn, 162Dy, 52Cr, and 56Fe.

Fluorescent Compounds:
Other Labels:

As known in the art any distinguishable component may be covalently linked or attached in any manner to the agent for detection in a sample such as fluorescent dye etc.

Kits

In still further embodiments, the present invention concerns kits for use with the methods and comparison methods described herein. One or more distinguishable agent(s) provided in a kit may be employed to assess organ health in a health facility and/or a home kit format. Distinguishable agent(s) such as a hepatic blood flow assessing agent and/or hepatic metabolism assessing agent (e.g. cholate and/or caffeine respectfully) may thus comprise, a suitable container means, an oral dose of distinguishable agent to possibly be administered outside of a hospital environment. In addition, a second IV dose may be administered in a healthcare facility. Sample tubes for collection of the bodily fluid samples such as blood or saliva for collection either inside or outside a healthcare facility may also be included. In one example, a kit may comprise an oral and an IV dose of one or more distinguishable agents and sample tubes for collection of samples over a period of less than 3 hours after administration of the distinguishable agents. In another example, a kit may comprise components necessary for a test period of 30 minutes post administration of distinguishable agents.

Another kit may include distinguishable metabolic indicators of hepatic health such as distinguishable caffeine. It is also contemplated that a combination kit having both a metabolic indicator such as caffeine and a hepatic blood flow indicator such as cholate may be useful to assess overall hepatic health of a subject.

Further suitable reagents for use in the present kits include the two-component reagent that comprises a distinguishable agent detection system and a metabolic function detection system. The kits may further comprise a suitably aliquoted composition of the specific agent such as cholate, whether labeled or unlabeled, as may be used to prepare a standard curve for a detection assay.

The container means of the kits will generally include at least one vial, test tube, flask, bottle, syringe or other container means, into which the distinguishable agent may be placed, and preferably, suitably aliquoted. The kits of the present invention will also typically include a means for containing the distinguishable agent and any other reagent containers in close confinement for commercial sale. Such containers may include injection or blow-molded plastic containers into which the desired vials are retained. In addition, the kits may contain a product for diluting the distinguishable oral agent such as a fruit juice or other liquid.

Example Procedure for Performance of Quantitative Clearance Tests
Supplies
IV Test Compounds
IV Solution B—30% Galactose (e.g. Pfanstiehl Laboratories)
IV Solution C—13C-Cholate (20 mg) (e.g. CDN Isotopes)
IV Test Compound supplied ready to use in Test Kit
IV Solution A—2% Lidocaine (e.g. Abbott Laboratories)
PO (Per Oral) Test Compounds
2H4-Cholate (40 mg) (e.g. CDN Isotopes)
Caffeine (300 mg) (e.g. Ruger)
Antipyrine (500 mg) (e.g. Ruger)
Sodium bicarbonate (e.g. 600 mg)
Patient Testing Supplies
25% Human Albumin for injection (5 mls) to be added to 13C-Cholate solution
Serum/plasma transfer tubes and labels
Saliva collection tubes and labels
Patient Testing Supplies
IV supplies, including 250 mls NS, indwelling catheter, 3-way stopcock
3 cc, 5 cc, 10 cc, and 50 cc syringes for administering IV test compounds and drawing blood samples
7 cc red top and 7 cc gray top vacutainer tubes for serum sample collections
Needle discard bucket
A drinking substance such a apple or grape juice for diluting oral test compounds One standard caffeine-free meal with one can Ensure for Liver-Spleen Scan Example Patient Preparation Ascertain whether patient has history of allergic reactions to local anesthetics (such as at the dentist), or history of cardiac arrhythmias; if so, do not administer lidocaine.
Patient is caffeine-free for 72 hours prior to test day and for the subsequent 3 days of saliva collections.
Patient is NPO except water after MN the night before test day.
Patient has IV with 3-way stopcock and NS TKO placed before test begins.

Exemplary Test Compound Preparation

One exemplary solution of an oral composition may contain 2H4-Cholate Caffeine, Antipyrine, and Sodium bicarbonate (e.g. 40 mg. 300 mg, 500 and 600 mg respectively) In one exemplary method, the day before the test, water can be added to about the 10 cc mark on a tube containing the oral test compounds. Cap tube tightly and shake to mix. Swirl contents to get all the powder granules down into the water.

On the test day pour dissolved Oral Test Solution into a container such as a urine cup. Rinse tube into urine cup with about 10 mls water. Prior to beginning the test, add a diluting liquid such as grape or apple juice (not citrus juice) to about the 40 ml mark on the urine cup containing the Oral Test Solution. Swirl gently to mix; do not shake or stir, or mixture may foam out of container. Have extra juice on hand for rinse.

IV Solution A (2% Lidocaine)
2% Lidocaine in a pre-packaged single-use 5 cc syringe as part of the Test Kit may be provided.
Test dose is 0.5 mg Lidocaine/kg.
Calculate appropriate dose of Lidocaine.

EXAMPLE

Divide the patient's weight in pounds by 2.2 to get kilograms; i.e., 150 lbs/2.2=68.2 kg
Multiply the weight in kg by 0.5 mg/kg to get the Lidocaine dose; i.e., 68.2 kg×0.5=34.3 mg
Divide the desired mg by 20 (concentration of 2% Lidocaine in mg/ml) to get cc's; i.e., 34.3 mg/20=1.71 cc
Expel excess Lidocaine from the 5 cc syringe so that it contains the correct dose. IV Solution B (100 cc 30% Galactose)
Galactose is prepared in individual doses for IV. A preparation procedure may be provided. Test dose is 30 gm Galactose, or 100 mls of 30% Galactose solution.
One example IV Solution and one application of a solution, IV Solution A (20 mg 13C-Cholate in 5 cc 1 mEq/ml Sodium Bicarbonate+5 cc 25% Human Albumin)
13C-Cholate can be prepared in individual 5 cc doses for IV. A preparation procedure may be provided. See Appendix C.
Test dose is 20 mg 13C-Cholate (in 10 cc diluent).
If vial is frozen, allow to thaw completely before continuing.

Just prior to beginning test, mix 13C-Cholate solution with albumin as follows (this method prevents loss of test compound during mixing process):

Draw up all of 13C-Cholate solution (about 5 cc) in a 10 cc syringe.

Draw up 5 cc albumin in another 10 cc syringe. Inject this gently (to prevent foaming) into empty 13C-Cholate vial, invert vial to rinse, then withdraw all of the albumin back into same syringe. (This rinses all of the 13C-Cholate out of the vial.)

Detach needle from the 13C-Cholate syringe and attach a 3-way stopcock. Detach needle from albumin syringe and inject albumin through stopcock into 13C-Cholate syringe.

Draw a little air into bile acid/albumin syringe and mix solutions gently by inverting syringe several times. Expel air.

Example Testing Procedure

In one exemplary method the following procedure will be used:

Collect baseline saliva and serum samples (see Sample Collection) before test compounds are given.

Administration of Test Compounds

Start timer. Record 24-hour clock time as T=0.

0 to 2 minutes—using 3-way stopcock, administer IV Solution A (1 mg/kg 2% Lidocaine) IV push. Record timer time.

2 to 3 minutes—allow NS to flush line for 1 minute.

3 to 8 minutes—using 3-way stopcock, administer IV Solution B (100 ml bolus 30% Galactose) IV push. Record timer time.

8 to 9 minutes—allow NS to flush line for 1 minute.

8 to 9 minutes—while line is flushing, have patient drink oral solution of test compounds and juice. Rinse cup with a little more juice and have patient drink rinse.

9 to 10 minutes—using 3-way stopcock, administer IV Solution A (20 mg Bile Acid in 5 mls 1 mEq/ml Sodium Bicarbonate+5 mls 25% Human Albumin) IV push. Record timer time.

Example of Sample Collection for Cholate and other compounds

Blood

Collect all samples via the 3-way stopcock with 0.5 ml discard before each sample to prevent dilution or cross-contamination of samples.

Collect 7 ml in colored tubes like red tops for 13C-Cholate Clearance (IV Solution C) at the following times (time after administration/timer time):

Baseline (before test compounds administered), 5/15, 10/20, 15/25, 20/30, 30/40, 45/55, 60/70, 75/85, 90/100, 105/115, 120/130, 150/160, and 180/190 minutes.

Collect 7 ml in a different colored cap tube like gray tops for Galactose Clearance (IV Solution B) at the following times, also using same timer started at T=0 (time after administration/timer time):

Baseline (before test compounds administered), 20/28, 40/48, 60/68, and 80/88 minutes.

Collect 10 ml red tops for MEGX Concentration (Lidocaine IV Solution A) at the following times, (time after administration/timer time):

Baseline (before test compounds administered), 15/17, and 30/32 minutes.

Keep gray top tubes on ice or refrigerated. Allow red tops to clot at room temperature for at least 30 minutes. Spin all samples for 15 minutes. Transfer plasma (gray)/serum (red) to appropriate labeled tubes and freeze at −20C. until shipping. Ship frozen.

Saliva

Have patient rinse mouth with water before each sample collection, then stimulate saliva production by chewing parafilm squares.

Collect 5 cc saliva (foam does not count) by spitting into labeled collection tube.

Collect at the following times:

Baseline, and 6, 12, 24, 36, 48, and 60 hours

Patient may collect samples at home for convenience. If so, instruct patient regarding saliva collections at home, freezing at home, and returning samples to site. Give patient supplies for home collection.

Cap tubes tightly and freeze at −20C until shipping. Ship frozen.

Liver/Spleen Scan

After completion of the blood sample collections (T=190) and 1 hour before Liver-Spleen Scan, give subject standard, caffeine-free meal.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

In one exemplary method, two hundred eighty five patients enrolled in a trial (called the HALT-C trial; Hepatitis Antiviral Long-Term Treatment to Prevent Cirrhosis Trial) and participated in a QLFT (quantitative liver function test) ancillary study. Seventy three patients were studied twice.

Example Patient Protocol: 20 mg of 24-13C cholic acid was dissolved in NaHCO3, mixed with 5 ml 25% human albumin solution and injected through an indwelling intravenous catheter over 2 minutes. 40 mg of 2,2,4,4-2H cholic acid was dissolved in water, mixed in juice and taken orally simultaneously with the intravenous injection. Blood samples were drawn through the indwelling catheter and taken prior to isotope administration and 5, 10, 15, 20, 30, 45, 60, 75, 90, 105, 120, 150 and 180 minutes post-dose to obtain oral and intravenous cholic acid clearance curves.

Sample Preparation:

In one example, dispense 0.5 ml patient serum and add 50 ul of Cholic acid standard, set aside two Cholic acid controls. To each tube add 0.5 ml distilled water and 0.5 ml 0.02 N NaOH. Mix and incubate in a 60-degree water bath for 30 minutes. Prepare Bond Elute paks (C18-OH) by washing with 5 mls methanol and 10 mls water. Add patient sample to pak. Wash paks with 5 mls distilled water, 5 mls 13% methanol and 5 mls 87% methanol. Dry sample completely. Add 1.5 ml water to dried residue, 1 drop HCL and 2 ml of diethyl ether. Vortex for 30 seconds. Centrifuge for 5 minutes to clarify layers. Collect ether layer in small, screw-capped, silanized test tubes. Repeat this step. Evaporate ether in 30-degree water bath under stream of nitrogen. Methylate samples by adding 1 ml methanol, 1 ml DMP and 1 drop HCL and incubate at room temperature in the dark for 30 minutes. Evaporate solvent at 40 degrees in water bath under a stream of nitrogen. Make trimethylsilyl ether derivatives of bile acids by adding 0.2 ml pyridine, 8 drops HMDS and 4 drops TMCS and incubate 55-60 degrees for 2 hours. Evaporate solvents under nitrogen stream. Add 2 ml hexane. Centrifuge for 5 minutes and pour off hexane. Repeat this step. Evaporate solvent and reconstitute with 4 drops hexane. Vortex and sonicate, then transfer to injection vials. Inject onto GC/MS 6890/5973 using method Cholic2.m.

Example 2

Statistical Analysis

In one example, one analysis was to determine if exogenously ingested and iv administered distinguishable agents are a marker for hepatic conditions not simply an affirmative or negative test for hepatic conditions.

Example Study

In one example, 7 QLFTs may be used to define hepatic impairment in patients with chronic hepatitis C and bridging fibrosis or compensated cirrhosis enrolled in the Hepatitis Antiviral Long-Term Treatment to Prevent Cirrhosis Trial (HALT C). Test results can be used to compare those with or without biopsy-proven cirrhosis, splenomegaly on ultrasonography, and varices at endoscopy.

In one example study the mean age of the 248 enrolled patients was 49.9+7.3 yr and 75% were male. Mean BMI (body mass index) was 29.6+5.3, 40% had cirrhosis, 60% had bridging fibrosis, 93% were infected with HCV genotype 1, and mean serum HCV RNA was 4.39+4.66×106 copies/ml. 30% had platelet count <140,000/ul, 25% had albumin <3.5 g/dl, 25% had INR >1.1 (international normalization ratio prothrombin), 10% had bilirubin >1.2 mg/dl, and 25% had AST:ALT >1 (serum aspartate transaminase: serum alanine transaminase).

In accordance with this example: 13C-methionine (MBT), caffeine (Caf), antipyrine (AP), and 2,2,4,4-2H-cholate (CA) were taken orally and 24-13C-cholate, galactose (Gal), and lidocaine were administered intravenously. These compounds or their metabolites were measured from timed serial samples of blood, saliva, and breath using standard techniques. Elimination rate (kelim), volume of distribution (Vd), clearance (Cl), elimination capacity (Elim), and shunt were calculated from measured analytes. Perfused hepatic mass (PHM) was determined from SPECT liver scan. Mean test results were compared by T statistic and area under the receiver operator curve (ROC) by C statistic. Table results are ordered by T statistic for association with cirrhosis. PHM had the highest area under ROC with cirrhosis (C statistic 0.87), splenomegaly (C statistic 0.75), and varices (C statistic 0.832) and correlated best with platelet count, bilirubin, prothrombin time, and albumin.

The outcome of the exemplary process was that QLFTs uncover hepatic impairment in a high proportion of fibrotic patients with chronic hepatitis C. Some of the tests, particularly CA Cloral, PHM, and CAshunt, identify patients with chronic hepatitis C with cirrhosis, splenomegaly or varices.

In one example, long-term follow-up, may be planned in the HALT C trial in order to determine whether hepatic impairment as defined by QLFTs predicts risk for clinical deterioration.

Standard Laboratory Tests

Standard laboratory tests (complete blood count, liver biochemistry profile) per routine clinical care of the post-hepatectomy donor at each center and per the prospective A2ALL Cohort Study donor protocols. In addition, specific study-related tests will be obtained at times of QLFT testing (baseline, 5 to 10 days, 3 months, and 6 months). The latter tests can include:

Complete Blood Count
Liver biochemistry profile (6 month only; others are already included in Cohort Study)
Body weight
BMI
Medication history (all)
Recording of any clinical events at 6-month time point
Exemplary Computing Device for Data Analysis FIG. 1 illustrates an exemplary computing device 100 that can carry out the operations described herein in accordance with various embodiments of the present invention. The exemplary computing device 100 is illustrative of many different types of computing devices such as, but not limited to, a general-purpose computer, a special-purpose computer, web server, and a handheld computer. It is to be understood that embodiments of the present invention are not limited to the particular computing device 100 shown in FIG. 1.

In one embodiment, the computing device 100 is in operable communication with a mass spectrometer, which generates chromatographic data. The chromatographic data can then be transmitted to the computing device 100. In another embodiment, the computing device 100 can download chromatographic data from a network resource. In yet another embodiment, chromatographic data can be input to the computer via a memory medium, such as a disk. Still another embodiment allows for the chromatographic data to be manually entered into the computing device 100 (e.g., via keyboard).

In this simplified example, the computing device 100 comprises a bus or other communication means 101 for communicating information, and a processing means such as one or more processors 102 coupled with bus 101 for processing information. Computing device 100 further comprises a random access memory (RAM) or other dynamic storage device 104 (referred to as main memory), coupled to bus 101 for storing information and instructions to be executed by processor(s) 102. Main memory 104 also may be used for storing temporary variables or other intermediate information during execution of instructions by processor(s) 102. Computing device 100 also comprises a read only memory (ROM) and/or other static storage device 106 coupled to bus 101 for storing static information and instructions for processor 102. A data storage device 107 such as a magnetic disk or optical disc and its corresponding drive may also be coupled to bus 101 for storing information and instructions.

One or more communication ports 110 may also be coupled to bus 101 for allowing communication and exchange of information to/from with the computing device 100 by way of a Local Area Network (LAN), Wide Area Network (WAN), Metropolitan Area Network (MAN), the Internet, or the public switched telephone network (PSTN), for example. The communication ports 110 may include various combinations of well-known interfaces, such as one or more modems to provide dial up capability, one or more 10/100 Ethernet ports, one or more Gigabit Ethernet ports (fiber and/or copper), or other well-known interfaces, such as Asynchronous Transfer Mode (ATM) ports and other interfaces commonly used in existing LAN, WAN, MAN network environments. In any event, in this manner, the computing device 100 may be coupled to a number of other network devices, clients and/or servers via a conventional network infrastructure, such as a company's Intranet and/or the Internet, for example.

Exemplary Operations for Data Analysis

Figure 4:
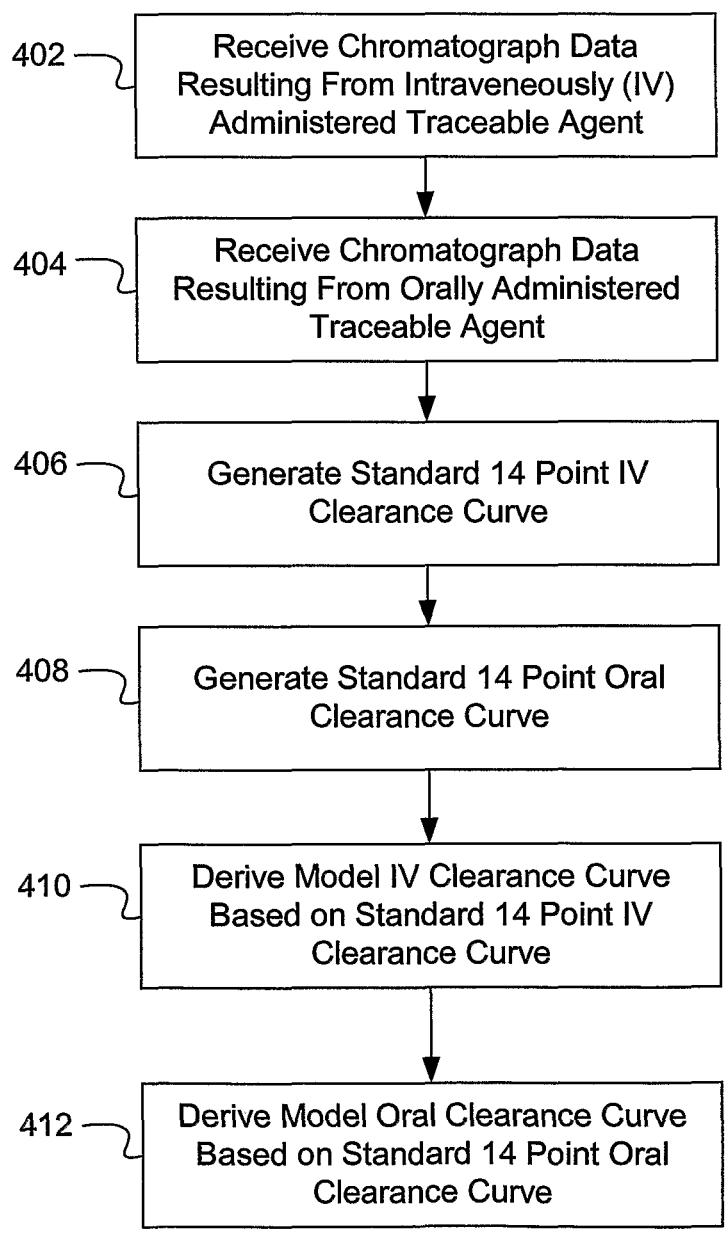
FIG. 4 illustrates a flow chart of an exemplary model curve derivation algorithm 400 having exemplary operations for generating a model clearance curve in accordance with one embodiment of the present invention.

FIG. 4 illustrates an exemplary model curve derivation algorithm 400 having exemplary operations for deriving a model clearance curve in accordance with a particular embodiment of the present invention. The algorithm 400 can be carried out by the computing device 100 shown in FIG. 1. Alternatively, the algorithm 400 could be carried out by a device other than the computing device 100. Prior to describing the algorithm 400 in detail, some general aspects of distinguishable agents and clearance of agents from blood for example are discussed.

Figure 2:
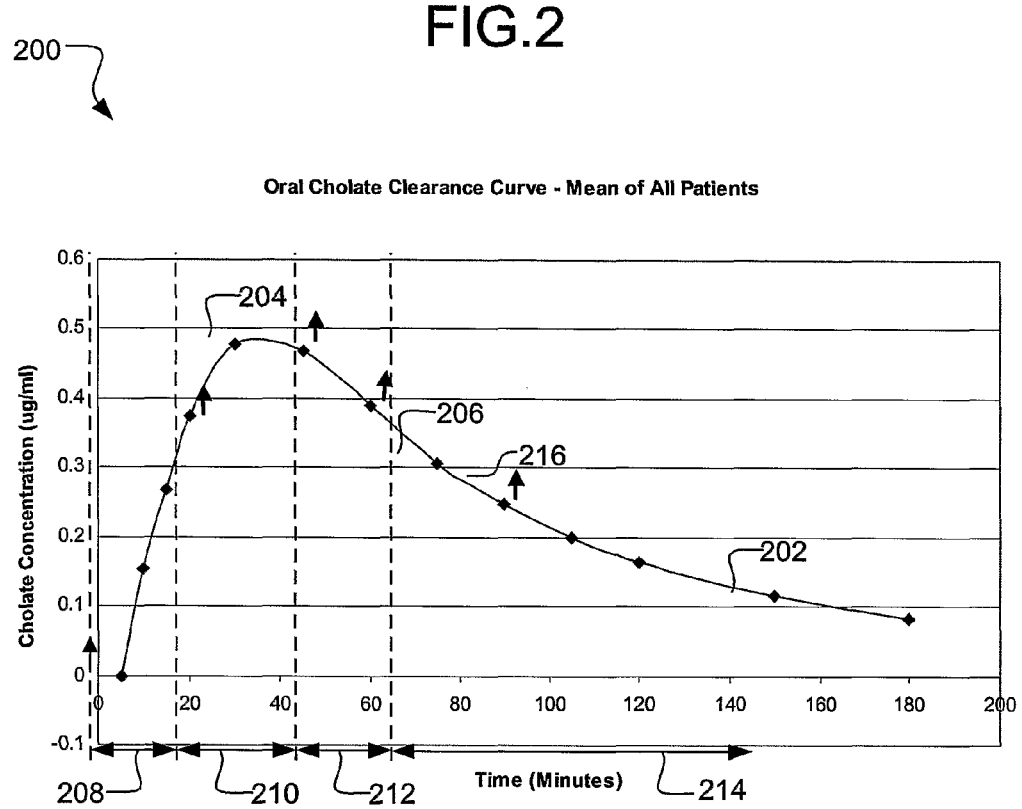
FIG. 2 illustrates a standard clearance curve derived from a sampling of over 300 patients administered cholate orally.
Figure 3:
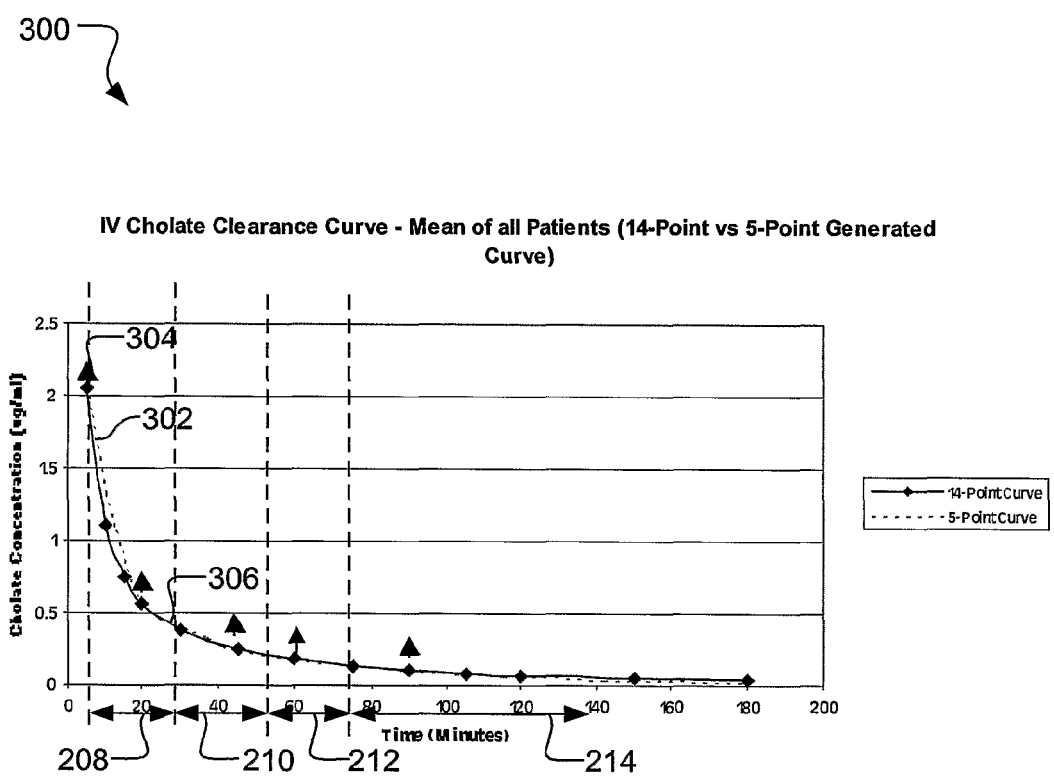
FIG. 3 illustrates a standard clearance curve derived from samples of over 300 patients administered cholate intravenously.

With regard to clinical testing with the use of a distinguishable agent, analysis typically involves determining clearance of the agent from a bodily fluid or sample such as the blood over time. Clearance generally refers to reduction or elimination of an agent concentration in the sample. The clearance can be graphically depicted with an agent concentration curve, which plots the concentration of the agent with respect to time. For a given agent, the concentration generally follows a similar curve for different patients. FIGS. 2 and 3 illustrate standard clearance curves that were derived from a sample of over 300 patients who were administered cholate orally (FIG. 2) and intravenously (FIG. 3). In this example, fourteen blood samples were taken from each of the patients to derive the standard clearance curves.

Referring to FIG. 2, the standard oral clearance curve 202 has characteristics (e.g., shape) that are generally similar among clearance curves derived from patients who have ingested cholate. For example, the clearance curve 202 can generally be characterized by a gradual increase in concentration, followed by an exponential decrease. Inflection points 204 and 206 are evident in the clearance curve 202. The general shape of the clearance curve 202 is characteristic of many agents in addition to cholate. As such, generally clearance curves derived from any administered agent such as an oral administration may include inflection points and the general shape as those shown in FIG. 2.

As another example, FIG. 3 is a graph 300 of a clearance curve 302 associated with intravenously (IV) administered cholate. The clearance curve 302 for IV administered cholate is characterized by sudden maximum concentration 304 around several minutes, followed by exponential decline in the concentration. An inflection point 306 generally occurs sometime during the exponential decline. The general shape of the clearance curve 302 is typical for most agents that are administered intravenously. As used herein, an IV clearance curve refers to a clearance curve associated with intravenous administration of an agent, and an oral clearance curve refers to a clearance curve associated with oral administration of an agent.

Although intravenous clearance curves for different agents share the same general shape and oral clearance curves for different agents share the same general shape, they typically differ in some ways. For example, the times at which inflection points occur can differ for different agents. In addition, the maximum values for agent concentrations can differ. Also, elimination rates can vary. However, because the clearance curves have the same general shapes for different agents, useful model clearance curves can be derived that can be used for conducting tests. Beneficially, such models can reduce the number of blood samples that need to be taken from the patients.

With the foregoing in mind, a process can be employed to identify characteristics associated with standard clearance curves for a distinguishable agent that is administered to a patient. These characteristics can be used to derive model clearance curves for future tests involving the agent. Turning to FIG. 4, the exemplary embodiment of algorithm 400 derives model characteristic curves for IV administered agent and orally administered agent based on selected times associated with characteristics (e.g., inflection points, slope, etc.) of standard IV and oral clearance curves. Although algorithm 400 is described with respect to cholate, those skilled in the art will recognize that the general process described can be readily adapted to other agents.

In a particular embodiment, prior to executing the algorithm 400, it is assumed that several hundred patients are each administered cholate orally and intravenously. At selected times after the administration of the cholate, blood samples are taken from each of the patients. In accordance with this embodiment, fourteen blood samples may be taken from each of the patients. However, the number of blood samples taken is not limited to fourteen and may be less or more than fourteen depending on the application. The fourteen blood samples per patient will be used to derive a standard fourteen point IV clearance curve and a standard fourteen point oral clearance curve. The blood samples are then prepared to obtain data that is input into the algorithm 400.

Example Blood Preparation:

In accordance with a particular embodiment, preparing the blood samples can include applying the following steps to each of the blood samples:

1. Dispense 0.5 ml patient serum and add 50 µl of cholic acid standard, set aside two Cholic acid controls.
2. To each tube add 0.5 ml distilled water and 0.5 ml 0.02 N NaOH.
3. Mix and incubate in a 60-degree water bath for 30 minutes.
4. Prepare Bond Elute paks (C18-OH) by washing with 5 mls methanol and 10 mls water.
5. Add patient sample to pak.
6. Wash paks with 5 mls distilled water, 5 mls 13% methanol and 5 mls 87% methanol.
7. Dry sample completely.
8. Add 1.5 ml water to dried residue, 1 drop HCL and 2 ml of diethyl ether.
9. Vortex for 30 seconds.
10. Centrifuge for 5 minutes to clarify layers.
11. Collect ether layer in small, screw-capped, silanized test tubes.
12. Repeat step 11.
13. Evaporate ether in 30-degree water bath under stream of nitrogen.
14. Methylate samples by adding 1 ml methanol, 1 ml DMP and 1 drop and incubate at room temperature in the dark for 30 minutes.
15. Evaporate solvent at 40 degrees in water bath under a stream of nitrogen.
16. Make trimethylsilyl ether derivatives of bile acids by adding 0.2 ml pyridine, 8 drops HMDS and 4 drops TMCS and incubate 55-60 degrees for 2 hours.
17. Evaporate solvents under nitrogen stream. Add 2 ml hexane.
18. Centrifuge for 5 minutes and pour off hexane.
19. Repeat step 18.
20. Evaporate solvent and reconstitute with 4 drops hexane.
21. Vortex and sonicate, then transfer to injection vials.
22. Inject onto mass spectrometer and instruct mass spectrometer to analyze prepared samples searching for ions associated with cholate.

In one embodiment, step 22 employs gas chromatography mass spectography (GC/MS). For example, a 6890/5973 mass spectrometer from AGILENT TECHNOLOGIES, INC may be used. However, other mass spectrometers may be used. For example, in other embodiments, high pressure liquid chromatography mass spectography (HPLCMS) is employed. The mass spectrometer is instructed (e.g., programmed) to monitor the prepared samples for ions specific to the particular agent of interest. In the embodiment described, the mass spectrometer is programmed to monitor for ions specific to cholate. In one embodiment, the ions monitored are specific to mass fragments of the agent. However, in other embodiments, other types of ions are monitored. The choice of which ions to monitor is dependant upon various factors related to the process, including, but not limited to, the molecular size of the agent and how the agent is derivatized.

After the samples are prepared, a receiving operation 402 receives the chromatographic data from the mass spectrometer related to intravenously administered cholate. Another receiving operation 404 receives chromatograph data related to orally administered cholate. In one embodiment of the algorithm 400, each of the receiving operations 402 and 404 receives fourteen data points representing an average of data from fourteen prepared blood samples.

A generating operation 406 generates a standard fourteen point IV clearance curve based on the received IV data. Another generating operation 408 generates a standard fourteen point oral clearance curve based on the received oral data. Those skilled in the art will readily recognize how standard fourteen point clearance curves can be generated in the generating operations 406 and 408.

Figure 5:
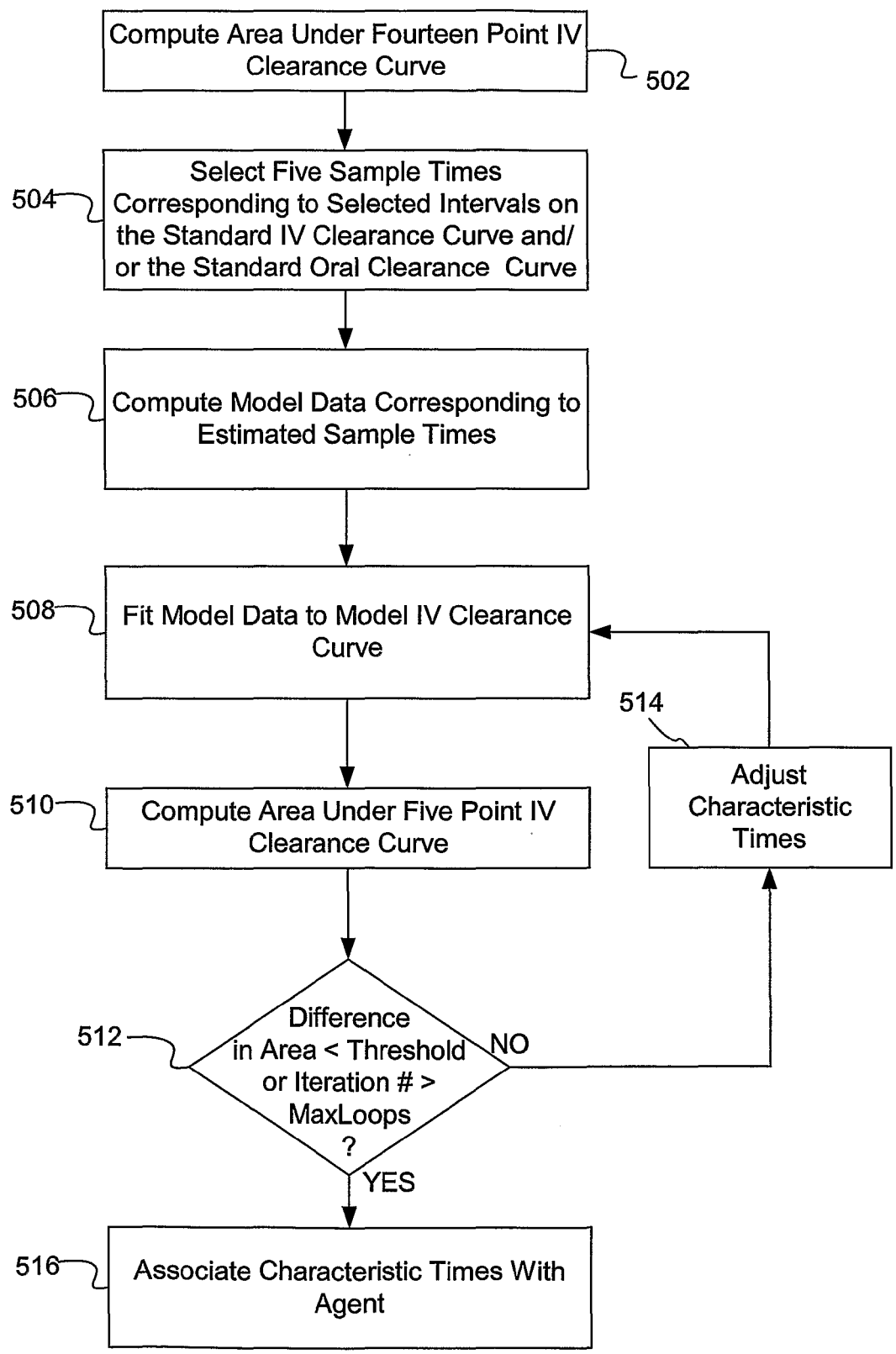
FIG. 5 illustrates a flow chart of an exemplary model IV clearance curve derivation algorithm 500 for generating a model IV clearance curve based on a standard 14 point IV clearance curve.
Figure 6:
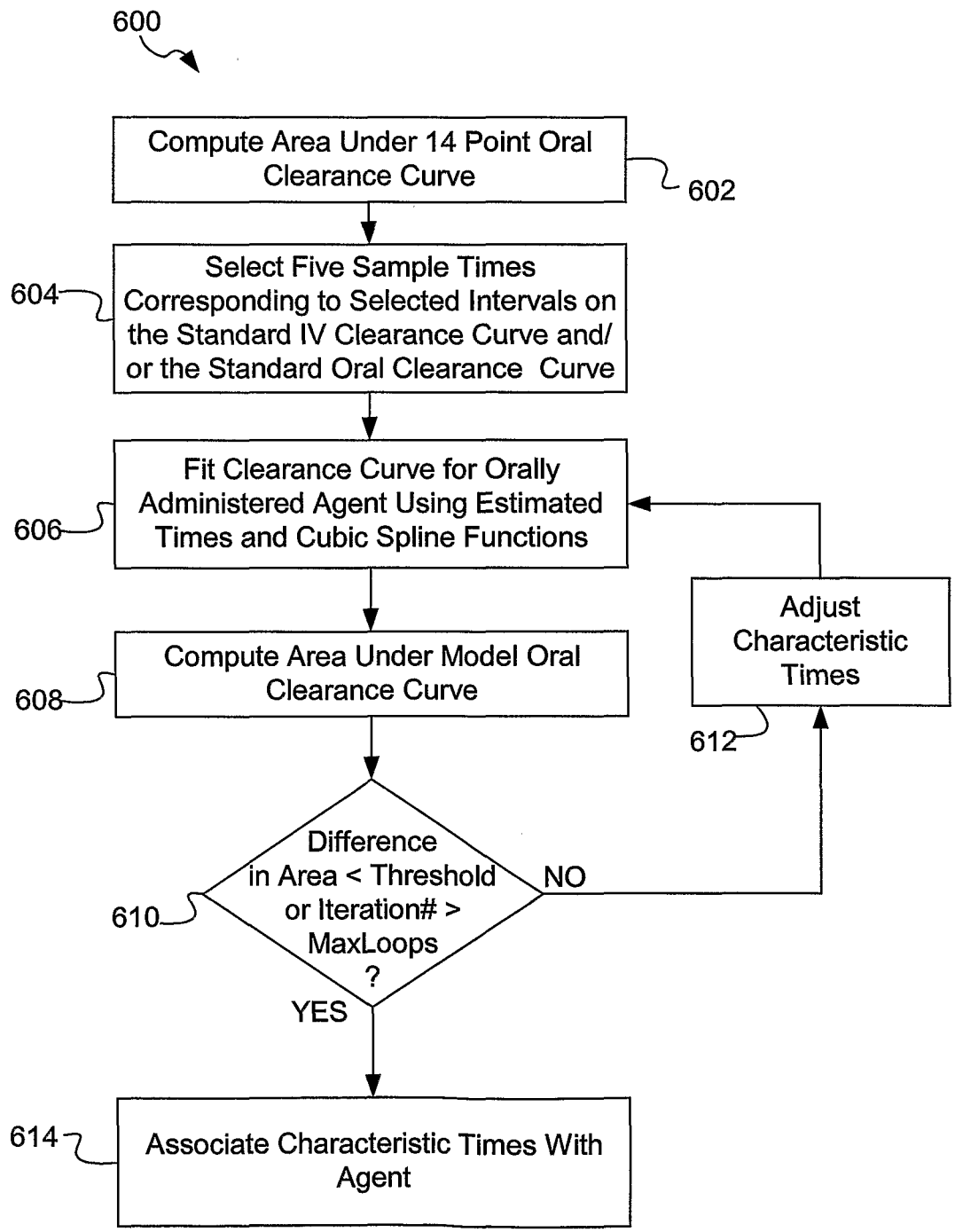
FIG. 6 illustrates a flow chart of an exemplary embodiment of an algorithm for deriving a model oral clearance curve based on a standard fourteen point oral clearance curve.

A deriving operation 410 derives a model IV clearance curve based on the standard fourteen point IV clearance curve. Another deriving operation 412 derives a model oral clearance curve based on the standard fourteen point oral clearance curve. Generally, the deriving operations 410 and 412 generate model data based on selected data points among the fourteen data points and fit the model data to a curve, referred to as a model clearance curve. An embodiment of the deriving operation 410 is shown in FIG. 5 and discussed in detail below. An embodiment of the deriving operation 412 is shown in FIG. 6 and is discussed in detail below.

As discussed, FIG. 5 illustrates a model IV clearance curve derivation algorithm 500 for deriving a model IV clearance curve based on a standard 14 point IV clearance curve. Referring to FIG. 5, initially the area under the 14 point IV clearance curve is computed in computing operation 502. Computing the area under a curve is generally understood by those skilled in the art. For example, area can be computed using known software programs, such as, but not limited to, EXCEL (MICROSOFT CORP.) or MATLAB (THE MATHWORKS, INC.). Alternatively, area can be computed using a proprietary program. A selecting operation 504 selects sample times corresponding to selected intervals on the standard fourteen point IV clearance curve and/or the standard fourteen point oral clearance curve. In one embodiment of the selecting operation 504, five sample times are selected. In other embodiments, more or fewer than five sample times can be selected. The selecting operation 504 can be carried out manually or automatically. In one embodiment, selecting manually involves visually observing the standard 14 point clearance curve and selecting times within intervals between characteristic points, such as inflection points. To illustrate, the oral clearance curve 202 in FIG. 2 includes four intervals: first interval 208, second interval 210, third interval 212, and fourth interval 214. In FIG. 2, the selected times are indicated by arrow markers 216. As shown in this particular embodiment, times at 5 minutes, 20 minutes, 45 minutes, 60 minutes, and 90 minutes are selected.

In a computing operation 506, model data is computed that will be used to generate the model clearance curve. In one embodiment of the computing operation 506, agent elimination rates are computed that correspond to each interval shown in FIG. 3. In this embodiment, agent elimination rates are computed using an exponential function. Equation (1) represents an exponential function characteristic of the clearance curve 302 in FIG. 3:

$$C_t = C_0 e^{-kt}, \quad \text{Eq. (1)}$$

wherein $C_t$ represents the concentration of the agent at time 't', and 'k' represents the elimination rate.

For each interval, the exponential can be expressed as in Equation (2):

$$C_{t_{i+1}} = C_{t_i} e^{-k(t_i - t_{i+1})}, \quad \text{Eq. (2)}$$

wherein 'i' represents an interval.
Using Equation (2), the elimination rate for each interval can be expressed as:

Eq. (3) Using Equation (2), the elimination rate for each interval can be expressed as:

$$k_i = \ln\left(\frac{C_{t_{i+1}}}{C_{t_i}}\right) / (t_i - t_{i+1}). \quad \text{Eq. (3)}$$

In a particular embodiment, four times, 5, 20, 45, and 90, are selected for the IV model clearance chart. Each of the selected times corresponds to one of the intervals. Corresponding elimination rates are shown below. To determine the first elimination rate, k1, Eq. (3) is simultaneously solved for t1=5 minutes and t2=20 minutes resulting in Eq. (4):

$$k_1 = \ln\left(\frac{C_{20}}{C_5}\right) / (t_1 - t_2) \quad \text{Eq. (4)}$$

To determine the second elimination rate, $k_2$, Eq. (3) is simultaneously solved for $t_3$=45 minutes and $t_4$=90 minutes resulting in Eq. (5):

$$k_2 = \ln\left(\frac{C_{90}}{C_{45}}\right) / (t_3 - t_1) \quad \text{Eq. (5)}$$

To determine the function of the model clearance curve between $t_2$=20 minutes and $t_3$=45 minutes, a third elimination rate, $k_3$, can be solved in the same manner as above resulting in Eq. (6):

$$k_3 = \ln\left(\frac{C_{45}}{C_{20}}\right) / (t_2 - t_3). \quad \text{Eq. (6)}$$

In a fitting operation 508, the elimination rates are used to fit a curve based on five points obtained from the fourteen received IV points. In one embodiment, the fitting operation 508 substitutes the computed elimination rates, k1, k2, and k3 into Eq. (1) above for each interval in order to create a model IV clearance curve.

A computing operation 510 computes the area under the model IV clearance curve that was fitted in the fitting operation 508. Any of various area computation methods may be used as discussed above with respect to the computing operation 502.

After the area is computed for the model IV clearance curve, a determining operation 512 determine whether the area under the model IV clearance curve is within a predetermined range of the area under the standard 14 point IV clearance curve. In one embodiment, the difference between the two areas is computed. The difference in areas is then compared to a specified threshold. The specified threshold can be set to any value that is applicable to the particular application.

If the determining operation 512 determines that the area under the model IV clearance curve is not within the predetermined range of the area under the standard 14 point IV clearance curve, the algorithm branches 'NO' to an adjusting operation 514. The adjusting operation 514 adjusts the estimated sample times in a manner to make the two computed areas closer in value. The adjusting operation 514 can be carried out manually or in an automated fashion.

If the determining operation 512 determines that the area under the model IV clearance curve is within the predetermined range of the area under the standard 14 point IV clearance curve or the algorithm 500 has looped more than MaxLoops times, the algorithm branches 'YES' to an associating operation 516, which associates the selected times with the distinguishable agent that was intravenously administered. MaxLoops is a specified value that is chosen to ensure that looping eventually stops and sample times are associated with the distinguishable agent.

FIG. 6 is an embodiment of an algorithm 600 for deriving model oral clearance curve based on a standard 14 point oral clearance curve. Initially computing operation 602 computes the area under the standard 14 point oral clearance curve. An selecting operation 604 then selects sample times based on the standard 14 point oral clearance curve. One embodiment of the selecting operation 604 selects five sample times; however, in other embodiments, the number of sample times may be more or fewer than five sample times.

The estimated five times are generally based on characteristics (e.g., inflection points) of the standard 14 point oral clearance curve. The selecting operation 604 can be carried out manually or in an automated fashion. In some embodiments, the selecting operation 604 can select the times derived in the model IV clearance curve derivation 500.

A fitting operation 606 then fits a model clearance curve for the orally administered cholate using the five sample times determined in the selecting operation 604. One implementation of the fitting operation 606 employs a cubic spline function, as shown in Eq. (7):

$$f_i(t) = \frac{f''(t_{i-1})}{6(t_i - t_{i-1})}(t_i - t)^3 +$$

$$\frac{f''(t_i)}{6(t_i - t_{i-1})}(t - t_{i-1})^3 + \left[\frac{f(t_{i-1})}{t_i - t_{i-1}} - \frac{f''(t_{i-1})(t_i - t_{i-1})}{6}\right]$$

$$(t_i - t) + \left[\frac{f(t_i)}{t_i - t_{i-1}} - \frac{f''(t_i)(t_i - t_{i-1})}{6}\right](t - t_{i-1}),$$

Eq. (7)

wherein $f_i(t)$ represents the model clearance curve function during interval 'i' with respect to time, 't'.

Eq. (7) are two unknown second derivatives, f'', for each interval. To solve for the two unknown second derivatives, Eq. (7) can be differentiated to give an expression for the first derivative for both the (i−1)th and the ith intervals. Then the two results can be set equal, assuming that the first derivatives at contiguous points on the clearance curve are continuous:

$$f'_{i-1}(t_i) = f'_i(t_i)$$

Eq. (8)

The following relationship results:

$$(t_i - t_{i-1})f''(t_{i-1}) + 2(t_{i+1} - t_{i-1})f''(t_i) + (t_{i+1} - t_i)f''(t_{i+1}) =$$

$$\frac{6}{t_{i+1} - t_i}[f(t_{i+1}) - f(t_i)] + \frac{6}{t_i - t_{i+1}}[f(t_{i-1}) - f(t_i)]$$

Eq. (9)

Also noting the second derivatives at the endpoints are 0, four equations and four unknowns can be written and solved for all unknown second derivatives. After the second derivatives are solved for, complete spline functions could be generated for all 4 intervals. Using the above cubic spline equations, the model oral clearance curve is generated for intervals 208, 210, 212, and interval 214 up to t=90 minutes. (FIG. 2). To generate the portion of the model oral clearance curve after 90 minutes, an exponential function is used. In one embodiment, the exponential function after 90 minutes is derived by computing the average 'k' elimination rate for all sample patients. The average 'k' elimination rate is then used in Eq. (1) to generate the remaining portion of the model oral clearance curve. This average 'k' elimination rate is the same k elimination derived from the IV clearance curve. In this case, the IV and oral clearance curves decay at the same rate.

After the model oral clearance curve is generated, a computing operation 608 computes the area under the model oral clearance curve. A determining operation 610 determines whether the area under the model oral clearance curve is within a predetermined range of the area under the standard 14 point clearance curve. If the difference between the two areas is not less than a specified threshold, the algorithm 600 branches 'NO' to an adjusting operation 612. The adjusting operation 612 adjusts the sample times to make the two area values closer in value. After the times are adjusted, the fitting operation 606 again fits the model data to a model oral clearance curve.

Figure 7:
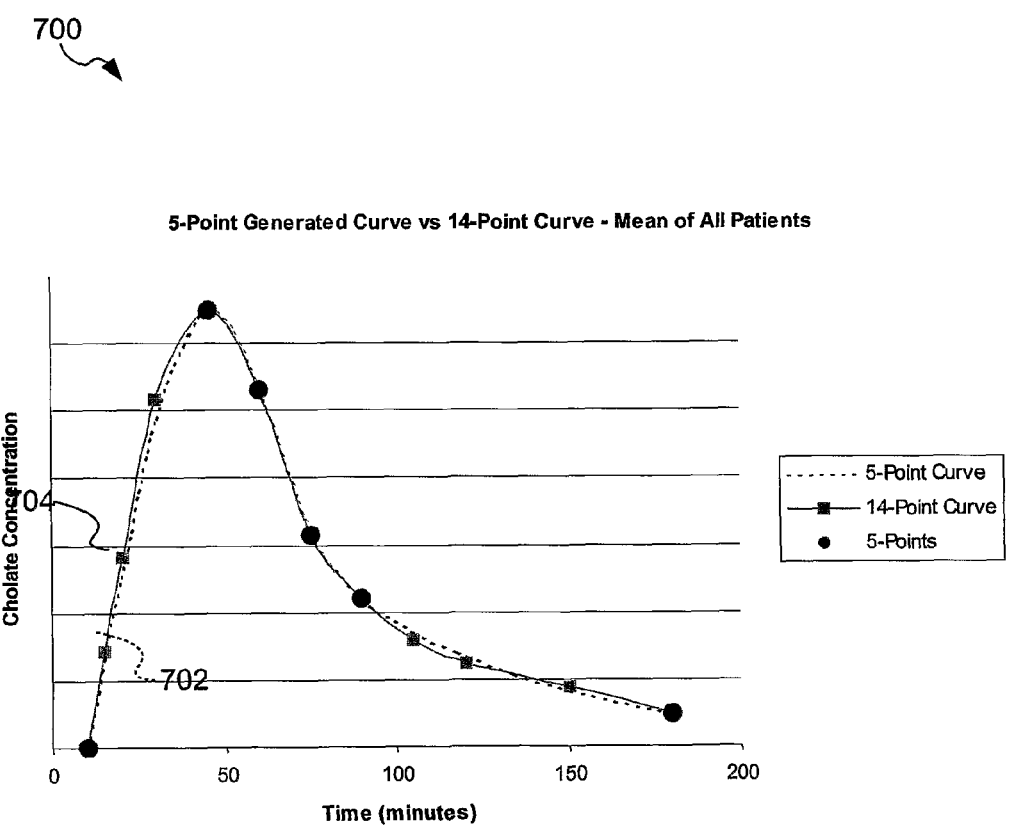
FIG. 7 illustrates a standard clearance curve derived from a sampling of over 300 patients showing a model five point oral clearance curve and a standard fourteen point clearance curve from which the model curve was derived.

If the determining operation 610 determines that the area under the model oral clearance curve and the standard 14 point clearance curve are within the predetermined threshold or the algorithm 600 has looped more than MaxLoops times, the algorithm 600 branches 'YES' to an associating operation 614. The associating operation 614 associates the five selected times with the distinguishable agent. FIG. 7 is an exemplary graph 700 showing a model five point oral clearance curve 702 (dotted line) and a standard 14 point clearance curve 704 (solid line) from which the model curve 702 was derived. Thus, in future tests, the patient may only need to provide blood samples at less selected times such as five selected times (e.g., 5, 20, 45, 60, and 90 minutes), and, using the model oral clearance curve 702, an individualized clearance curve can be generated for the patient.

To calculate the liver shunt fraction, the exponential decay equations and the spline function equations, generated mathematically by the 5 selected points, are integrated along their respective valid time ranges and an area is generated. The liver shunt fraction is then calculated:

$$ShuntFraction = \left[\frac{AUC_{oral}}{AUC_{IV}}\right] * \left[\frac{Dose_{IV}}{Dose_{oral}}\right] * 100\%,$$

Eq. (10)

wherein AUC represents Area under the curve and Dose represents the amount (in mg) of dose administered.

The model IV clearance curve derivation algorithm 500 and the model oral clearance curve derivation algorithm 600 may be carried out together. For example, in some embodiments, the algorithms 500 and 600 are carried out in serial. In other embodiments, the algorithms 500 and 600 are carried out in parallel. By carrying out the two algorithms together, the sample times for both the IV clearance curve and the oral clearance curve can be selected so that they are equal. In addition, the order of operations described in FIGS. 5-6 are not limited by the orders shown. In some embodiments, operations may be carried out in different orders, and operations may be merged or separated without straying from the scope and spirit of the claimed invention.

Example 3

An Exemplary Clinical and Biochemical Endpoint Study of Disease Progression. In one example study, two long term studies examined rates of disease progression in patients with HCV with bridging fibrosis and cirrhosis. One study used these estimates to calculate samples sizes for the current NIH treatment trial based upon an equal distribution of noncirrhotic and cirrhotic patients. Disease progression can be defined herein as an increase in fibrosis score of 2 points or more, or development of hepatic decompensation, death from liver disease, or HCC. The following table represents a total sample size that would be required to achieve 90% power for a binomial chi-square test with a two-sided alpha of 0.05.

|  | A | B | C | D |
|---|---|---|---|---|
| Control (%/yr) | 4.0 | 5.0 | 6.0 | 7.0 |
| Control (%/4 yr) | 15.1 | 18.5 | 21.9 | 25.2 |
| 50% decrease in Endpoints |  |  |  |  |
| IFN (%/yr) | 2.0 | 2.5 | 3.0 | 3.5 |
| IFN (%/4 yr) | 8.7 | 10.8 | 12.8 | 14.9 |
| N for 90% power | 1084 | 870 | 728 | 626 |
| Noncompliance (5%/yr) |  |  |  |  |
| IFN (%/4 yr) | 9.3 | 11.5 | 13.6 | 15.8 |
| N for 90% power | 1324 | 1064 | 890 | 767 |

During the first 6 months of therapy, all patients can be treated and control and maintenance therapy groups experience disease progression at the same rate. If the control group has an annual clinical event rate of 7% (column D), then 25.2% will have developed a clinical event by the end of four years. If maintenance treatment reduces the annual rate by 50% and if treatment is started after 6 months, then the event rate will be 14.9% at the end of four years. If 5% of the treated group become noncompliant each year, then the event rate required to maintain significance would be 15.8% at the end of four years. Approximately 1200 patients will need to be enrolled into the trial to achieve statistical significance for the primary endpoint. The ability of the study to determine efficacy for maintenance therapy would be compromised if either the rate of development of clinical endpoints is lower than projected or if rates of dropout from the trial exceed 5%/yr.

Example 4

Use of Multiple QLFTs in Other Populations (the HALT C Study)

In one example, seven QLFTs were used to define hepatic impairment in patients with chronic hepatitis C and bridging fibrosis or compensated cirrhosis enrolled in the Hepatitis Antiviral Long-Term Treatment to Prevent Cirrhosis Trial (HALT C). These results can be compared to those with or without biopsy-proven cirrhosis, splenomegaly on ultrasonography, and varices at endoscopy (10).

The mean age of the 248 enrolled patients was 49.9+7.3 yr and 75% were male. Mean BMI was 29.6±5.3, 40% had cirrhosis, 60% had bridging fibrosis, 93% were infected with HCV genotype 1, and mean serum HCV RNA was 4.39±4.66×10$^6$ copies/ml. 30% had platelet count <140,000/µl, 25% had albumin <3.5 g/dl, 25% had INR >1.1, 10% had bilirubin >1.2 mg/dl, and 25% had AST:ALT >1.

13C-methionine (MBT), caffeine (Caf), antipyrine (AP), and 2,2,4,4-2H-cholate (CA) were taken orally and 24-13C-cholate, galactose (Gal), and lidocaine were administered intravenously. These compounds or their metabolites were measured from timed serial samples of blood, saliva, and breath using standard techniques. Elimination rate (kelim), volume of distribution (Vd), clearance (Cl), elimination capacity (Elim), and shunt were calculated from measured analytes. Perfused hepatic mass (PHM) was determined from SPECT liver scan. Mean test results were compared by T statistic and area under the receiver operator curve (ROC) by C statistic. Table results are ordered by T statistic for association with cirrhosis.

| % of Pts with | | Cirrhosis | | Splenomegaly | | Varices | |
|---|---|---|---|---|---|---|---|
| Test | Abnl Test | T-Stat | P | T-Stat | P | T-Stat | P |
| CA Cloral | 70% | 7.74 | .0000 | 3.32 | .0010 | 3.97 | .0001 |
| PHM | 65% | 6.92 | .0000 | 3.93 | .0002 | 4.95 | .0000 |
| CA Shunt | 75% | −6.73 | .0000 | −3.65 | .0003 | −3.81 | .0002 |
| Caf kelim | 48% | 3.78 | .0002 | 2.33 | .0207 | 1.09 | NS |
| AP kelim | 82% | 3.61 | .0004 | 2.56 | .0116 | 2.09 | .0399 |
| MBT Score | 67% | 2.87 | .0046 | 3.46 | .0007 | 2.43 | .0169 |
| CA kelim | 38% | 2.86 | .0047 | 1.25 | NS | 2.36 | .0195 |
| Gal Elim | 73% | 2.58 | .0106 | 3.87 | .0001 | 2.28 | .0240 |
| AP Cl | 58% | 2.44 | .0160 | 1.37 | NS | 1.84 | NS |
| MEGX 15 min | 75% | 1.33 | NS | 1.91 | .0572 | 1.88 | NS |
| MEGX 30 min | 67% | 1.01 | NS | 1.77 | NS | 1.01 | NS |

PHM had the highest area under ROC with cirrhosis (c-statistic 0.87), splenomegaly (c-statistic 0.75), and varices (c-statistic 0.832) and correlated best with platelet count, bilirubin, prothrombin time, and albumin.

QLFTs may uncover hepatic impairment in fibrotic patients with chronic hepatitis C, and some tests, particularly CA Cloral, PHM, and CAshunt, identify patients with chronic hepatitis C with cirrhosis, splenomegaly or varices. Long-term follow-up may determine whether hepatic impairment as defined by QLFTs predicts risk for clinical deterioration.

Example 5

Cholate Clearance and Portal Shunt (Blood Flow)

The following example includes multiple tests to assess hepatic function by the tests listed below. These can include measurement of blood flow with cholate clearance, portal shunt with dual isotope cholate, and microsomal function with antipyrine clearance, caffeine clearance, MEGX formation from lidocaine and erythromycin breath test. Trough (C1) and peak (C2) concentrations of TAC and MMF concentrations at trough, 1 h, and 2 h post-dose, relative to dose, can be measured in all recipients. Volumetric studies can be performed using MRI, and functional mass will be measured using the SPECT liver-spleen scan.

Administration and Measurement of Test Compounds

Cholate clearance and portal shunt (blood flow): Intravenous 13C-cholate, for example 20 mg, can be dissolved in NaHCO3 solution, passaged through a micropore filter, and placed in sterile, capped glass vials prior to use. This preparation is mixed with 5 ml of 25% human albumin solution just prior to intravenous injection. The 2H4-cholate, for example 40 mg, is taken orally. Blood samples for measurement of cholate isotopes can be obtained at baseline and 5, 10, 15, 20, 30, 45, 60, 75, 90, 105, 120, 150, and 180 minutes post-dose (14 samples, 7 ml red top tubes). Serum concentrations of cholate are determined by GC/MS-isotope ratiometry (21). Comparison of intravenous and oral clearance curves allows determination of first-pass hepatic elimination or portal shunt (12, 22).

Other examples of tests used in combination with the cholate clearance test:

Antipyrine and caffeine clearances: Saliva samples, for measurement of antipyrine, can be obtained at baseline and at 6, 12, 24, 36, 48, and 60 hours post-dosing (e.g. 7 samples, mls each). Salivary concentrations of antipyrine and caffeine are measured by HPLC.

Erythromycin breath test: Breath samples for measurement of $14CO_2$ from the metabolism of 14C-erythromycin are obtained prior to and 20 minutes after IV administration of 14C-erythromycin. Breath samples are analyzed for radioactivity by trapping exhaled $CO_2$ and liquid scintillation counting.

MEGX from lidocaine: Blood samples for measurement of MEGX from the metabolism of lidocaine are obtained prior to and over 1 hour after the IV administered dose of lidocaine (0.5 mg/kg). MEGX is measured by HPLC.

The data provided by the combination teats will be used to assess overall organ health and in particular hepatic health. All samples for the above clearance studies will be coded with a unique identifier, dated, and collection time, center, PI recorded and samples stored in tightly-capped vials, and shipped on dry ice to the analytical laboratory.

Example 6

Patients: 286 patients enrolled in HALT C trial and participating in the QLFT (quantitative liver function test) ancillary study. 73 patients were studied twice at different times.
Patient Protocol 20 mg of 24-13C cholic acid was dissolved in NaHCO3, mixed with 5 ml 25% human albumin solution and injected through an indwelling intravenous catheter over 2 minutes. 40 mg of 2,2,4,4-2H cholic acid was dissolved in water, mixed in juice and taken orally simultaneously with the intravenous injection. Blood samples were drawn through the indwelling catheter and taken prior to isotope administration and 5, 10, 15, 20, 30, 45, 60, 75, 90, 105, 120, 150 and less than 180 minutes post-dose to obtain oral and intravenous cholic acid clearance curves.

Deconvolutional analysis was performed on the 14-point intravenous and oral clearance curves to obtain the minimal amount of points and time period required to regenerate the full curves. In one example, 2 to 7 time points spanning time periods from 5 to 180 minutes were modeled. In one model, 5 time points bracketing inflection points in the clearance curves and encompassing a time period of 90 min. the curve closely reflected the curve formally requiring 14 points. This analysis indicates that cholate shunt may be accurately determined from 5 samples of blood obtained approximately 5, 20, 45, 60 and 90 minutes post dose. The accuracy of the 5-point coined a "minimal model" in measurement of cholate shunt was 98.1+1.4% of that calculated using all 14 time points.

Example 7

Deconvolutional Analysis on Clearance Curves of Simultaneously Administered Oral and Intravenous Doses of 2,2, 4,4-2H Cholate and 24-13C Cholate: Minimal Model to Determine First-Pass Hepatic Extraction of Cholate in Humans.

In one example, a study of patients with chronic hepatitis C were used and a mathematical model of cholate clearance curves was used to generate one minimal model necessary to accurately measure cholate shunt in humans.

Patients: As indicated previously, 286 patients enrolled in a trial (Halt-C trial) and participating in the QLFT (quantitative liver function test) ancillary study. 73 patients were studied twice at different times.

Methods: In one example, 20 mg of 24-13C cholic acid was dissolved in NaHCO3, mixed with 5 ml 25% human albumin solution and injected through an indwelling intravenous catheter over 2 minutes. 40 mg of 2,2,4,4-2H cholic acid was dissolved in water, mixed in juice and taken orally simultaneously with the intravenous injection. Blood samples were drawn through the indwelling catheter and taken prior to isotope administration and 5, 10, 15, 20, 30, 45, 60, 75, 90, 105, 120, 150 and 180 minutes post-dose to obtain oral and intravenous cholic acid clearance curves. Serum concentrations of 13C and 2H cholates were determined from 0.5 ml aliquots of serum. 1.5 μg of unlabelled cholate was added to each serum sample. The cholates were isolated by extraction from serum with Sep-Pak C18 cartridge, acidification, ether extraction, methylation, TMS derivatization, and capillary GC/MS isotope ratiometry. Cholate shunt was calculated as AUCoral (area under the curve)/AUCiv×Doseiv/Doseoral×100%.

Deconvolutional analysis was performed on a 14-point intravenous and oral cholic acid clearance curves to obtain the minimal amount of points required to accurately regenerate the 14-point curves. This analysis indicates that cholate shunt may be accurately determined from 5 samples of blood obtained at 5, 20, 45, 60 and 90 minute post-dose. These time points bracket inflection points in the clearance curves. Use of fewer samples or time points that fail to bracket inflection points diminishes the accuracy of measurement of cholate shunt. The "minimal model" defined by this analysis significantly reduces the number of samples and time commitment required to determine cholate shunt in man. This can improve patient comfort, compliance with testing, reduce human error in sample collection and analysis, reduce time and expense, and save resources.

Example 8

Clearance of caffeine depends upon specific hepatic metabolic pathways and its measurement, which quantitates liver metabolic function, requires multiple samples for up to 3 days. Herein a method for measuring deuterated isotopes of caffeine is described for determining clearance from single samples of serum.
Example Method In one example, a study was performed to analyze hepatic condition of HCV patients using a multi-isotope method for measurement of caffeine elimination (TIME test). Caffeine concentrations range from 0.1 to 6 μg/ml over 24 h after a single oral dose of 300 mg. Deuterated caffeine (D3 and D9), unlabeled caffeine, and phenacetin (500 ng/ml) were added to five separate samples of calf serum and extracted after alkalinization using methylene chloride. The methylene chloride layer was taken to dryness and reconstituted in 50 μl of acetone. Compounds were analyzed by GC-MS with an initial oven temperature of 40° C. for 0.55 min, increasing at 50°/min to 280°, held isothermally at 280° for 4 min, and quantified by selected ion monitoring (m/z 179, 194, 197, and 203) using calibration curves with phenacetin as internal standard.

Example Outcome: The correlation coefficients for the calibration curves were 0.995, 0.996 and 0.995 for unlabelled, D3 and D9 caffeines, respectively. X±SD and coefficients of variance (CV) for unlabeled caffeine (2800 ng/mL) and D3 & D9 (400 ng/mL each) were 2800±109, 3.9%; 411±18, 4.4%; and 385±16 ng/ml, 4.2%, respectively. Instrument precision was 99.50%, 99.38%, and 99.51%, respectively. These concentrations reflect expected concentrations in human serum 4 h after an oral dose of 300 mg of total caffeine at a molar ratio D3 (or D9): unlabeled caffeine of 1:7. X±SD, CV of unlabeled caffeine (600 ng/mL) and D3 & D9 (150 ng/mL each), were 539±61, 11%; 143±12, 8.4%; and 135±16 ng/mL, 12% with precision of 98.73%, 99.43% and 99.22%, respectively. These concentrations reflect expected concentrations in serum 24 h after an oral dose of 300 mg total caffeine with a molar ratio of D3 (or D9): unlabeled caffeine of 1:4. This example method accurately quantifies caffeine and deuterated isotopes over concentration ranges achieved after oral dosing with 300 mg caffeine.

A triple isotope method (TIME test) by performance of appropriate clinical testing of human subjects and compare the results to standard caffeine clearance assays can be evaluated as follows:

| Validation Study | | |
|---|---|---|
| Subjects: | Group 1: | Healthy controls (N = 10) |
| | Group 2: | HCV patients, Ishak fibrosis stage 0-2 (N = 10) |
| | Group 3: | HCV patients, Ishak fibrosis stage 4-6 (N = 10) |

Protocol A: Subjects are place on a caffeine-free diet for 3 days then admitted to a monitoring center such as GCRC. Baseline samples of blood, serum and saliva for measurement of for example caffeine, CBC, INR, Chemistry profile (creatinine, liver tests included), pregnancy test and a history and physical examination.
Administration of Caffeine and Caffeine Isotopes were as follows:

| Unlabelled | |
|---|---|
| Isotope 1 | Time = t1 |
| Isotope 2 | Time = t2 |
| Isotope 3 | Time = t3 |

Post-dose samples were obtained as Sample 1, 2, 3, 4 and 5.
Repeat the study (items 1-5 above) after washout, 24 h<washout <7 d.
Protocol B: Same as Protocol A, but no caffeine-free diet.
Methods:
1. Addition of phenacetin as internal standard
2. Extraction of caffeine and caffeine isotopes from samples
3. Standard caffeine analysis by HPLC
4. Caffeine isotopes measured by GC/MS or HPLC/MS
Calculations:
1. Multiple sampling: Ln/linear regression of [caffeine] vs time.
Slope=elimination rate constant
Intercept yields [caffeine] at t=0, Vol of distribution calculated
Clearance product of elimination rate and vol of distribution.
2. Single samples (TIME test)
Each sample is analyzed for concentration of each of the 3 isotopes.
Sample time is difference between time of isotope admin and time of collection.
Ln/linear regression of [caffeine] vs time, yields elimination rate, vol dist, and Cl.
Statistics
1. Compare elim rate, vol dist, and Cl between standard and TIME methods, using Protocol A data.
2. Compare effect of dietary caffeine on both standard and TIME methods by comparing results for each method between Protocol A and Protocol B.
3. Define reproducibility of standard and TIME methods by comparing the initial and repeat studies done in both protocol A and protocol B.

The TIME test may be used alone or in combination with a cholate shunt test or other QLFTs to provide a comprehensive assessment of hepatic condition. Similarly, this test could be used to assess impact of disease, disease progression, therapies, interventions or transplantation.

After hepatic condition of a subject has been assessed it my be determined that a therapeutic treatment is necessary for the subject. Likely treatments or interventions in hepatic conditions include but are not limited to interferon, peginterferon, ribavirin, any new and emerging treatments for either or both hepatitis B and C, lamivudine, adefovir, tenofovir, telbivudine, ursodeoxycholic acid, treatments for NASH, TIPS, hepatic resection, hepatic transplantation.

All of the COMPOSITIONS and/or METHODS and/or APPARATUS disclosed and claimed herein can be made and executed without undue experimentation in light of the present disclosure. While the compositions and methods of this invention have been described in terms of preferred embodiments, it will be apparent to those of skill in the art that variation may be applied to the COMPOSITIONS and/or METHODS and/or APPARATUS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for quantitative assessment of portal-systemic shunt which defines both functional hepatic reserve and alteration of the portal circulation in a subject suspected of having or developing a hepatic disorder comprising:

intravenously administering to the subject at least one stable isotope distinguishable agent that is a conjugated or unconjugated bile acid; and orally administering to the subject at least a second stable isotope distinguishable agent that is a conjugated bile acid;

collecting blood samples from the subject over intervals of no more than 7 time points for a period consisting of no more than 180 minutes after administration of the agents to the subject;

measuring the ratio between the clearance as measured by AUC (AUC=area under the curve of the serum concentrations) of the at least one intravenously administered agent and the clearance as measured by AUC of the at least one orally administered agent, and comparing the ratio of clearance in the subject to the ratio of clearance from one or more normal healthy controls, or within the subject over time;

wherein the ratio of clearance of the administered agents is an indicator of portal-systemic shunt in the subject.

2. The method of claim 1, wherein administration of the intravenous stable isotope distinguishable agent; and administration of the oral stable isotope distinguishable agent to a subject comprises simultaneous administration of the intravenous and the oral distinguishable agents.

3. The method of claim 1, wherein the intravenously administered stable isotope distinguishable agent and the orally administered stable isotope distinguishable agent each comprises an unconjugated bile acid.

4. The method of claim 3, wherein the intravenously administered stable isotope distinguishable bile acid and the orally administered stable isotope distinguishable bile acid each comprises cholate.

5. The method of claim 4, wherein measuring the ratio between at least one intravenously administered agent and at least one orally administered agent in the samples comprises using a formula to calculate the cholate shunt value.

6. The method of claim 1, wherein at least one intravenously administered distinguishable agent and one orally administered distinguishable agent comprises at least one naturally occurring compound with a 50 percent or higher first pass elimination.

7. The method of claim 1, further comprising at least one additional hepatic assessment test.

8. The method of claim 7, wherein the hepatic assessment tests are quantitative liver function tests (QLFTs).

9. The method of claim 8, wherein the QLFT comprises a hepatic metabolic function test, a hepatic blood flow test or combination thereof.

10. The method of claim 9, wherein the hepatic metabolic function test is a multi-isotope caffeine test.

11. A method to assess the need for therapeutic treatment of a subject with a hepatic disorder comprising:

intravenously administering to the subject at least one stable isotope distinguishable agent that is a conjugated or unconjugated bile acid; and orally administering to the subject at least a second stable isotope distinguishable agent that is a conjugated or unconjugated bile acid to a subject suspected of having or developing a hepatic disorder;

collecting blood samples from the subject over intervals of no more than 7 time points for a period consisting of no more than 180 minutes after administration of the agents to the subject;

measuring the ratio between the clearance as measured by AUC (AUC=area under the curve of the serum concentrations) of the at least one intravenously administered agent and the clearance as measured by AUC of the at least one orally administered agent; and comparing the ratio of clearance in the subject to the ratio of clearance from one or more normal healthy controls, or within the subject over time;

wherein the ratio of the clearance of the administered agents is an indicator of a need for at least one therapeutic treatment of the subject with a hepatic disorder.

12. The method of claim 11, wherein distinguishable stable isotope agents are differentially labeled cholate and measuring the ratio comprises measuring the concentration of each of the differentially labeled cholate in a sample and calculating the cholate clearances and cholate shunt using the measurements.

13. The method of claim 11, wherein at least one therapeutic treatment comprises an antiviral therapy.

14. A method for measuring the progression of at least one hepatic condition in a subject comprising:

intravenously administering to the subject at least one stable isotope distinguishable agent that is a conjugated or unconjugated bile acid; and orally administering to the subject at least a second stable isotope distinguishable agent that is a conjugated or unconjugated bile acid to a subject suspected of having or developing a hepatic disorder;

collecting blood samples from the subject over intervals of no more than 7 time points for a period consisting of no more than 180 minutes after administration of the agents to the subject;

measuring the ratio between the clearance as measured by AUC (AUC=area under the curve of the serum concentrations) of the at least one intravenously administered agent and at the clearance as measured by AUC of the least one orally administered agent in the sample at a time after administration of the agents; and comparing the ratio of clearance in the subject to the ratio of clearance from one or more normal healthy controls, or within the subject over time;

wherein the ratio of the clearance of the administered agents is an indicator of the progression of at least one hepatic condition of the subject.

15. The method of claim 14, wherein the subject comprises a subject with chronic hepatitis C.

16. The method of claim 14, wherein the distinguishable agents comprise isotopically labeled cholate.

17. A method for quantitative assessment of portal-systemic shunt which defines functional hepatic reserve and alteration of the portal circulation in a subject comprising:

intravenously (IV) administering to the subject cholate isotopically labeled with $^{13}C$; and orally administering to the subject cholate isotopically labeled with $^{2}H$ to a patient with chronic hepatitis C;

collecting blood samples from the subject at various intervals of no more than 7 time points over a period consisting of no more than 90 minutes after administration of the cholate to the subject; and measuring the ratio between at least one intravenously administered cholate and at least one orally administered cholate in the sample using cholate clearance calculated from AUCoral/AUCiv×Doseiv/Doseoral×100% (AUC=area under the curve of the serum concentrations); and comparing the ratio of clearance in the subject to the ratio of clearance from one or more normal healthy controls, or within the subject over time;

wherein the ratio of the clearance of the cholate is an indicator of hepatic condition of the subject.

18. The method of claim 17, wherein the samples comprise blood samples at 5, 20, 45, 60 and 90 minutes post-dose.

19. The method of claim 17, further comprising administering at least one additional test to the subject that is an indicator of hepatic condition in a subject.

20. The method of claim 19, wherein at least one additional test is selected from the group consisting of clearance of aminopyrine, clearance of aminopyrine, clearance of antipyrine, clearance of bile acids other than cholate, clearance of caffeine, clearance of erythromycin, clearance of nitroglycerin, clearance of galactose, clearance of indocyanine green, clearance of lidocaine, clearance of midazolam, clearance of omeprazole, clearance of dextromethorphan, clearance of phenacetin, liver-spleen scan, serum bilirubin analysis, alanine aminotransferase analysis, aspartate aminotransferase analysis, alkaline phosphatase analysis or combination thereof.

21. A method to assess liver caffeine metabolism in a subject;
the method comprising:
administering two or more distinguishable caffeine solutions to a subject at different times, wherein each distinguishable caffeine is labeled with one or more distinguishable stable isotopes;
collecting salivary and/or blood samples at a single time point selected from the group consisting of 6, 12, 24, 36, 48 and 60 hours after administration of the solutions to the subject;
measuring distinguishable caffeine metabolites in the salivary and/or blood samples; and
comparing processing parameters of the two or more distinguishable caffeine solutions in a subject to a standard,
wherein the processing parameters of the administered caffeine solutions are an indicator of hepatic condition of the subject.

22. The method of claim 21, wherein administering distinguishable caffeine solutions comprises administering the solutions orally, intravenously or combination thereof.

23. The method of claim 21, wherein three distinguishable caffeine solutions are administered to a subject at different time intervals.

24. The method of claim 23, wherein a single sample is obtained sometime after administration of the distinguishable caffeine solutions to assess the hepatic condition of the subject.

25. The method of claim 21, further comprising administering at least one additional test to assess the hepatic condition of the subject.

26. The method of claim 25, wherein the at least one additional test comprises intravenously administering at least one distinguishable stable isotope of cholate; and orally administering at least a second distinguishable stable isotope of cholate to the subject.

27. The method of any of one of claim 1, 11, 14 or 17 wherein the collecting step occurs over intervals consisting of 5 time points.

28. The method of any one of claim 1, 11, or 14 wherein the collecting step occurs over a period consisting of no more than about 90 minutes.

* * * * *

UNITED STATES PATENT AND TRADEMARK OFFICE
CERTIFICATE OF CORRECTION

| | | |
|---|---|---|
| PATENT NO. | : 8,613,904 B2 | Page 1 of 1 |
| APPLICATION NO. | : 11/814793 | |
| DATED | : December 24, 2013 | |
| INVENTOR(S) | : G. T. Everson | |

It is certified that error appears in the above-identified patent and that said Letters Patent is hereby corrected as shown below:

In the Claims

In claim 1, Column 32, lines 59-60, the phase "isotope distinguishable agent that is a conjugated bile acid" should read:

--isotope distinguishable agent that is a conjugated or unconjugated bile acid--

Signed and Sealed this
Ninth Day of June, 2015

Michelle K. Lee
*Director of the United States Patent and Trademark Office*